US009215439B2

(12) United States Patent
Sudo

(10) Patent No.: US 9,215,439 B2
(45) Date of Patent: Dec. 15, 2015

(54) APPARATUS AND METHOD FOR ARRANGING EMAILS IN DEPTH POSITIONS FOR DISPLAY

(75) Inventor: Fukukyo Sudo, Nagano (JP)

(73) Assignee: SONY CORPORATION, Tokyo (JP)

(*) Notice: Subject to any disclaimer, the term of this patent is extended or adjusted under 35 U.S.C. 154(b) by 237 days.

(21) Appl. No.: 13/537,174

(22) Filed: Jun. 29, 2012

(65) Prior Publication Data

US 2013/0014024 A1 Jan. 10, 2013

(30) Foreign Application Priority Data

Jul. 6, 2011 (JP) .................................. 2011-150076

(51) Int. Cl.
*H04N 13/00* (2006.01)
*G06F 17/30* (2006.01)
*G06F 19/00* (2011.01)
(Continued)

(52) U.S. Cl.
CPC ........ *H04N 13/0018* (2013.01); *G06F 3/04815* (2013.01); *G06F 17/30061* (2013.01); *G06F 17/30126* (2013.01); *G06F 19/321* (2013.01); *H04N 13/0404* (2013.01); *H04N 13/0409* (2013.01); *H04N 13/0438* (2013.01)

(58) Field of Classification Search
CPC ... G06F 3/0481; G06F 3/0488; G06F 3/0425; G06F 3/04815; G06F 3/04883; G06F 3/1454; G06F 3/147; G06F 3/048; G06F 3/012; G06F 17/30061; G06F 17/30126; G06F 19/321; G06T 19/20; G06T 2200/24; G06T 2219/2004; G06T 2219/2016; G02B 27/2285; H04N 13/0029; H04N 13/0239

USPC .......................... 715/852, 836, 782, 848, 850
See application file for complete search history.

(56) References Cited

U.S. PATENT DOCUMENTS 6,121,969 A * 9/2000 Jain et al. ....................... 715/850
6,636,210 B1 * 10/2003 Cheng ........................... 345/419
(Continued)

FOREIGN PATENT DOCUMENTS

JP 10307936 A * 11/1998 .............. G06T 17/00
JP 2004-199142 A 7/2004
(Continued)

OTHER PUBLICATIONS

Advances in the Dynallax Solid-State Dynamic Parallax Barrier, Peterka et al., Jun. 2008.*

*Primary Examiner* — Ece Hur
(74) *Attorney, Agent, or Firm* — Hazuki International, LLC

(57) ABSTRACT

The information processing apparatus generates email information (or display contents) to be displayed on a display apparatus and outputs the generated email information to the display apparatus that is a 3D image display apparatus for displaying a 3D image observable by an observer on the basis of binocular parallax. The information processing apparatus updates the display contents to be displayed on the display apparatus in accordance with an operation input. The information processing apparatus outputs email information display (a first display state) or email information display (a second display state) from a display output block to the display apparatus. On the basis of an input operation, the information processing apparatus switches, through a switching block, a display state of the email information to be displayed on the display apparatus from the email information display (the first display state) to the email information display (the second display state).

13 Claims, 27 Drawing Sheets

(51) Int. Cl.
*G06F 3/0481* (2013.01)
*H04N 13/04* (2006.01)

(56) References Cited

U.S. PATENT DOCUMENTS

| | | | |
|---|---|---|---|
| 6,864,862 B2* | 3/2005 | Sato et al. | 345/32 |
| 8,826,432 B2* | 9/2014 | Dabbiere et al. | 726/22 |
| 2002/0140746 A1* | 10/2002 | Gargi | 345/853 |
| 2004/0070673 A1* | 4/2004 | Nakamura | 348/207.2 |
| 2004/0113915 A1* | 6/2004 | Ohtsuki et al. | 345/582 |
| 2004/0246199 A1* | 12/2004 | Ramian | 345/6 |
| 2005/0091596 A1* | 4/2005 | Anthony et al. | 715/712 |
| 2005/0134945 A1* | 6/2005 | Gallagher | 358/527 |
| 2005/0276416 A1* | 12/2005 | Zhu et al. | 380/210 |
| 2006/0075044 A1* | 4/2006 | Fox et al. | 709/206 |
| 2006/0193179 A1* | 8/2006 | England et al. | 365/185.22 |
| 2006/0209231 A1* | 9/2006 | Ioki et al. | 349/69 |
| 2007/0019884 A1* | 1/2007 | Jojic et al. | 382/284 |
| 2007/0150810 A1* | 6/2007 | Katz et al. | 715/526 |
| 2008/0094398 A1* | 4/2008 | Ng et al. | 345/427 |
| 2008/0120571 A1* | 5/2008 | Chang et al. | 715/810 |
| 2009/0021513 A1* | 1/2009 | Joshi et al. | 345/419 |
| 2009/0150772 A1* | 6/2009 | Noda et al. | 715/277 |
| 2009/0204920 A1* | 8/2009 | Beverley et al. | 715/768 |
| 2009/0307623 A1* | 12/2009 | Agarawala et al. | 715/765 |
| 2010/0039428 A1* | 2/2010 | Kim et al. | 345/419 |
| 2010/0050129 A1* | 2/2010 | Li et al. | 715/849 |
| 2010/0125814 A1* | 5/2010 | Lemons | 715/853 |
| 2010/0169823 A1* | 7/2010 | Audet | 715/784 |
| 2010/0272417 A1* | 10/2010 | Nagasawa et al. | 386/97 |
| 2010/0295929 A1* | 11/2010 | Yoshifuji et al. | 348/53 |
| 2011/0001746 A1* | 1/2011 | Kim et al. | 345/213 |
| 2011/0035681 A1* | 2/2011 | Mandel et al. | 715/752 |
| 2011/0179368 A1* | 7/2011 | King et al. | 715/769 |
| 2011/0205162 A1* | 8/2011 | Waller et al. | 345/173 |
| 2012/0044259 A1* | 2/2012 | Carlhian et al. | 345/629 |
| 2012/0092456 A1* | 4/2012 | Akiba | 348/46 |
| 2012/0117124 A1* | 5/2012 | Bruaset et al. | 707/797 |
| 2012/0124509 A1 | 5/2012 | Matsuda et al. | |
| 2012/0249529 A1* | 10/2012 | Matsumoto et al. | 345/419 |
| 2012/0256913 A1* | 10/2012 | Hamada | 345/419 |
| 2013/0063578 A1* | 3/2013 | Uesaka et al. | 348/53 |
| 2013/0070059 A1* | 3/2013 | Kushida | 348/47 |
| 2013/0083172 A1* | 4/2013 | Baba | 348/49 |
| 2013/0094833 A1* | 4/2013 | Fujita | 386/230 |
| 2013/0101263 A1* | 4/2013 | Morioka et al. | 386/224 |
| 2013/0169633 A1* | 7/2013 | Hattori et al. | 345/419 |
| 2015/0085074 A1* | 3/2015 | Kudo et al. | 348/45 |

FOREIGN PATENT DOCUMENTS

| | | | | |
|---|---|---|---|---|
| JP | 2005074094 A | * | 3/2005 | A63F 7/02 |
| JP | 2011-028309 A | | 2/2011 | |

* cited by examiner

| MAIL DISPLAY LINES | Message-ID | RECEPTION DATE | LAYER |
|---|---|---|---|
| 1 | Midxxx1 | y1/m1/d1 | L1 |
| 2 | Midxxx2 | y2/m2/d2 | L2 |
| 3 | Midxxx3 | y3/m3/d3 | L3 |
| 4 | Midxxx4 | y4/m4/d4 | L4 |
| 5 | Midxxx5 | y5/m5/d5 | L5 |
| 6 | Midxxx6 | y6/m6/d6 | L6 |
| 7 | Midxxx7 | y7/m7/d7 | L7 |
| 8 | Midxxx8 | y8/m8/d8 | L7 |
| 9 | Midxxx9 | y9/m9/d9 | L7 |
| 10 | Midxxx10 | y10/m10/d10 | L7 |

| LAYER | LEFT-EYE IMAGE CORRECTION VALUE | RIGHT-EYE IMAGE CORRECTION VALUE | FONT SIZE | BLUR EFFECT |
|---|---|---|---|---|
| L0 | 0 | 0 | 10 | 0 |
| L1 | -3 | 3 | 7 | 1 |
| L2 | -2 | 2 | 8 | 1 |
| L3 | -1 | 1 | 9 | 1 |
| L4 | 0 | 0 | 10 | 0 |
| L5 | 1 | -1 | 11 | 1 |
| L6 | 2 | -2 | 12 | 2 |
| L7 | 3 | -3 | 13 | 3 |

| EMAIL DISPLAY LINES | Message-ID | RECEPTION DATE | LAYER |
|---|---|---|---|
| 1 | Midxxx1 | y1/m1/d1 | L1 |
| 2 | Midxxx2 | y2/m2/d2 | L1 |
| 3 | Midxxx3 | y3/m3/d3 | L1 |
| 4 | Midxxx4 | y4/m4/d4 | L2 |
| 5 | Midxxx5 | y5/m5/d5 | L3 |
| 6 | Midxxx6 | y6/m6/d6 | L4 |
| 7 | Midxxx7 | y7/m7/d7 | L5 |
| 8 | Midxxx8 | y8/m8/d8 | L6 |
| 9 | Midxxx9 | y9/m9/d9 | L7 |
| 10 | Midxxx10 | y10/m10/d10 | L7 |

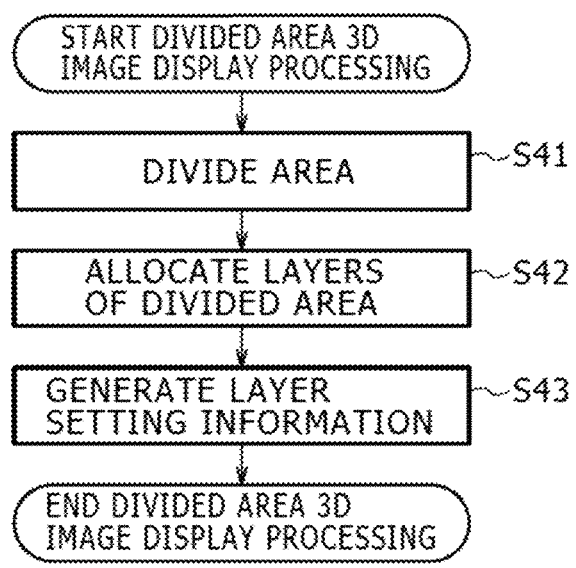

| LAYER | LEFT-EYE IMAGE CORRECTION VALUE | RIGHT-EYE IMAGE CORRECTION VALUE | FONT SIZE | BLUR EFFECT |
|---|---|---|---|---|
| L0 | 0 | 0 | 10 | 0 |
| L1 | 0 | 0 | 10 | 0 |
| L2 | -1 | 1 | 9 | 1 |
| L3 | -2 | 2 | 7 | 1 |
| L4 | -2 | 2 | 7 | 1 |
| L5 | -2 | 2 | 7 | 1 |

FIG.17

| LAYER | LEFT-EYE IMAGE CORRECTION VALUE | RIGHT-EYE IMAGE CORRECTION VALUE | FONT SIZE | BLUR EFFECT |
|---|---|---|---|---|
| 0 | 0 | 0 | 10 | 0 |
| 1 | 2 | -2 | 11 | 1 |
| 2 | 0 | 0 | 10 | 0 |
| 3 | -1 | 1 | 9 | 1 |
| 4 | -2 | 2 | 7 | 1 |
| 5 | -2 | 2 | 7 | 1 |

FIG.24

| | | 300 |
|---|---|---|
| DISPLAY OBJECT | | 001 |
| SHAPE | | WIDTH THICK WINDOW |
| SIZE | | MIDDLE |
| POSITION | | x1,y1,z1 |
| ORIENTATION | | dx1,dy1,dz1 |
| DISPLAY CONTENTS BY AREA | AREA a | OPERATION DISPLAY |
| | AREA b | FOLDER DISPLAY |
| | AREA c | LIST DISPLAY |
| | AREA d | PREVIEW DISPLAY |
| | AREA e | CAPACITY DISPLAY |
| | AREA f | OPERATION DISPLAY |

APPARATUS AND METHOD FOR ARRANGING EMAILS IN DEPTH POSITIONS FOR DISPLAY

CROSS-REFERENCE TO RELATED APPLICATION

The present application claims priority from Japanese Patent Application No. JP 2011-150076 filed in the Japanese Patent Office on Jul. 6, 2011, the entire content of which is incorporated herein by reference.

BACKGROUND

The present technology relates to an information processing apparatus, an image display apparatus, and an information processing method.

In related-art technologies, windows for example to be displayed on a screen of a display monitor are provided with shadows in order to enhance user visual effects in a desktop environment of a PC (Personal Computer), thereby creating three-dimensional (3D) visual effects.

In addition, recent display technologies can create stereoscopic effects based on binocular parallax as with 3D image display apparatuses for example. Based on these display technologies, an information processing apparatus was proposed in which a virtual object is arranged outside a display monitor display area in order to enhance not only user visual effects but also user processing efficiency (refer to Japanese Patent Laid-open No. 2011-28309).

SUMMARY

It should be noted however that the proposed information processing apparatus hardly provides the operability that is enough for significantly enhancing the processing efficiency for a user, thereby requiring the further improvement in the operability. With information processing apparatuses, the number of communication opportunities has remarkably increased with other users by means of email messages based on the significant development of networking. The email is now indispensable not only for business activities but also private activities, so that the ratio of the email processing time to the total work time has become so great as to be not ignorable. Consequently, the enhancement of the processing efficiency of the operation involved in email processing has become essential for the enhancement of the total work efficiency.

Therefore, the present disclosure addresses the above-identified and other problems associated with related-art methods and apparatuses and solves the addressed problems by providing an information processing apparatus, an image display apparatus, and an information processing method that are configured to significantly enhance user processing efficiency.

In carrying out the disclosure and according to one mode thereof, there is provided an information processing apparatus having a display output block, an input block, and a switching block. The display output block is configured to output email information display to a display apparatus on which a three-dimensional image is observable by an observer on the basis of binocular parallax. The input block is configured to receive a predetermined input operation. The switching block is configured to switch, on the basis of the input operation, display states of the email information display from a first display state to a second display state differing from the first display state in a depth position in the display apparatus.

In carrying out the disclosure and according to another mode thereof, there is provided an image display apparatus having a three-dimensional image display block, an input block, and a switching block. The three-dimensional image display block is configured to display email information in a three-dimensional image observable by an observer on the basis of binocular parallax. The input block is configured to accept a predetermined input operation. The switching block is configured to switch, on the basis of the input operation, display states of the email information from a first display state to a second display state differing from the first display state in a depth position in the image display apparatus.

In carrying out the disclosure and according to still another mode thereof, there is provided an information processing method. This information processing method has the steps of: outputting email information display to a display apparatus on which a three-dimensional image is observable by an observer on the basis of binocular parallax; receiving a predetermined input operation; and switching, on the basis of the input operation, display states of the email information display from a first display state to a second display state differing from the first display state in a depth position in the display apparatus.

According to the information processing apparatus, the image display apparatus, and the information processing method described above, the processing efficiency for a user is significantly enhanced.

BRIEF DESCRIPTION OF THE DRAWINGS

FIG. 13 is a flowchart indicative of divided-area 3D image display processing practiced as the third embodiment of the disclosure;

FIG. 14 is a diagram illustrating one example of layer allocation information practiced as the third embodiment of the disclosure;

FIG. 17 is a diagram illustrating one example of layer setting information obtained after the resetting practiced as the third embodiment of the disclosure;

FIG. 24 is a diagram illustrating one example of switching information practiced as the fifth embodiment of the disclosure;

DETAILED DESCRIPTION OF THE PREFERRED EMBODIMENTS

The present disclosure will be described in further detail by way of embodiments thereof with reference to the accompanying drawings.

The First Embodiment

Figure 1:
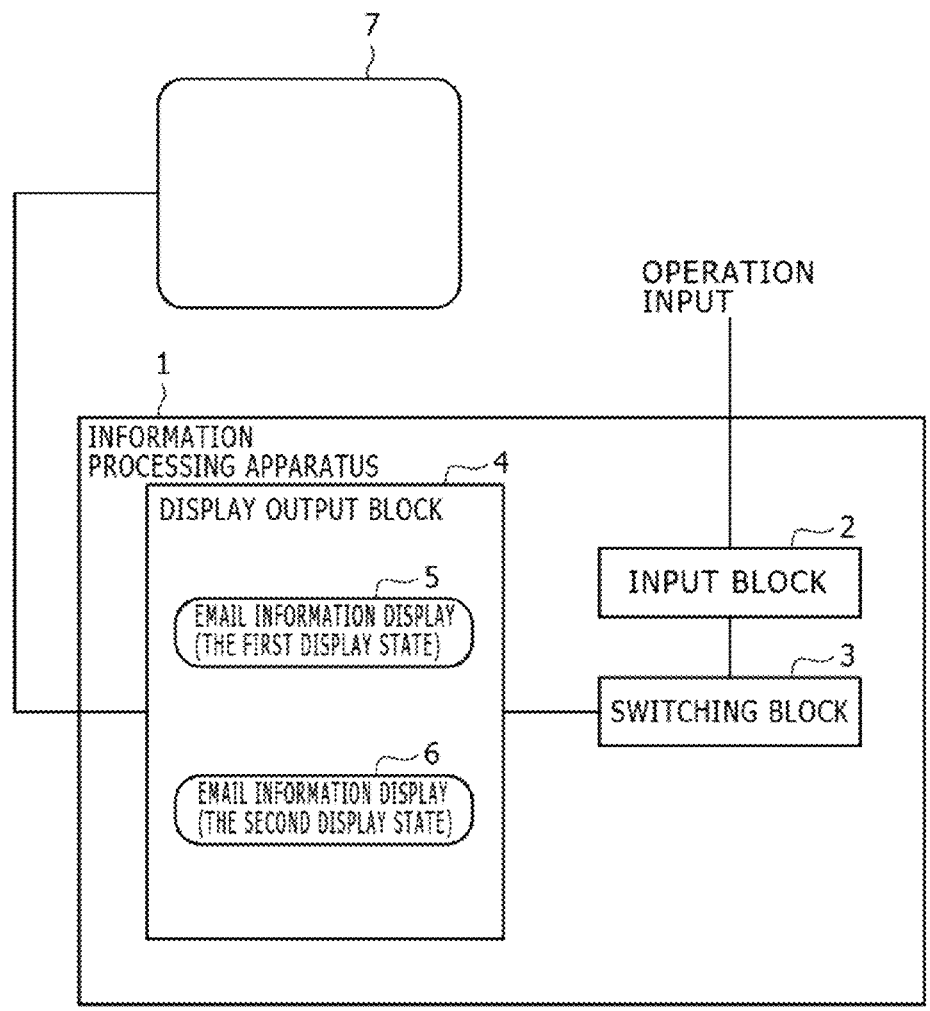
FIG. 1 is a schematic diagram illustrating an exemplary configuration of an information processing apparatus practiced as a first embodiment of the disclosure.

First, an information processing apparatus practiced as the first embodiment of the present disclosure will be described with reference to FIG. 1. Referring to FIG. 1, there is shown an exemplary configuration of the information processing apparatus practiced as the first embodiment of the present disclosure.

The information processing apparatus 1 generates email information (or display contents) to be displayed on a display apparatus 7 and outputs the generated email information to the display apparatus 7 that is a three-dimensional (or 3D) image display apparatus configured to display a 3D image observable by an observer on the basis of binocular parallax.

The information processing apparatus 1 has an input block 2, a switching block 3, and a display output block 4. The information processing apparatus 1 may be a personal computer that is separate from the display apparatus 7 or a so-called smart television that is unitized with the display apparatus 7, for example. Moreover, the information processing apparatus 1 may be portable such as a mobile phone or a game machine in addition to stationary such as mounted on a predetermined position (desktop or in-vehicle), for example.

The display output block 4 outputs an email information display (or a first display state) 5 or an email information display (or a second display state) 6 to the display apparatus 7. The email information displays 5 and 6 are email-associated information displays, such as email itself, email contents, email header information, email attribute information, operation information for manipulating email, and folder information for storing email, for example. The email information displays 5 and 6 are display contents to be displayed by a mailer (or an electronic email client) into a window thereof, for example. It should be noted that email messages to be displayed include short messages in addition to electronic email and web mail.

The email information display 5 is the first display state for displaying an email information display by a predetermined depth position. The email information display 6 is the second display state for displaying an email information display by a predetermined depth position different from that of the first display state. It should be noted that each email information display is made up of one or more display objects. The depth position of each display object may have a different depth position from each other.

The input block 2 receives a predetermined operation input. The input block 2 is an input device, such as a mouse, a keyboard, or a touch pad, for example. An operation input triggers the switching between the display states of an email information display. For example, operation inputs include a sort operation for switching between the display states of a mailer and attribute change operations such as making an email message already read and attaching a spam flag, for example.

The switching block 3 switches the display states of email information to be displayed on the display apparatus from the email information display 5 to the email information display 6 on the basis of a received input operation.

As described above, on the basis of a predetermined operation input, the information processing apparatus 1 can switch the display state of the email information to be displayed on the display apparatus 7 from the email information display 5 to the email information display 6. Consequently, the information processing apparatus 1 can provide an email handling environment that is more easily viewable and more easily operable, thereby enhancing the processing efficiency for the user.

The Second Embodiment

Figure 2:
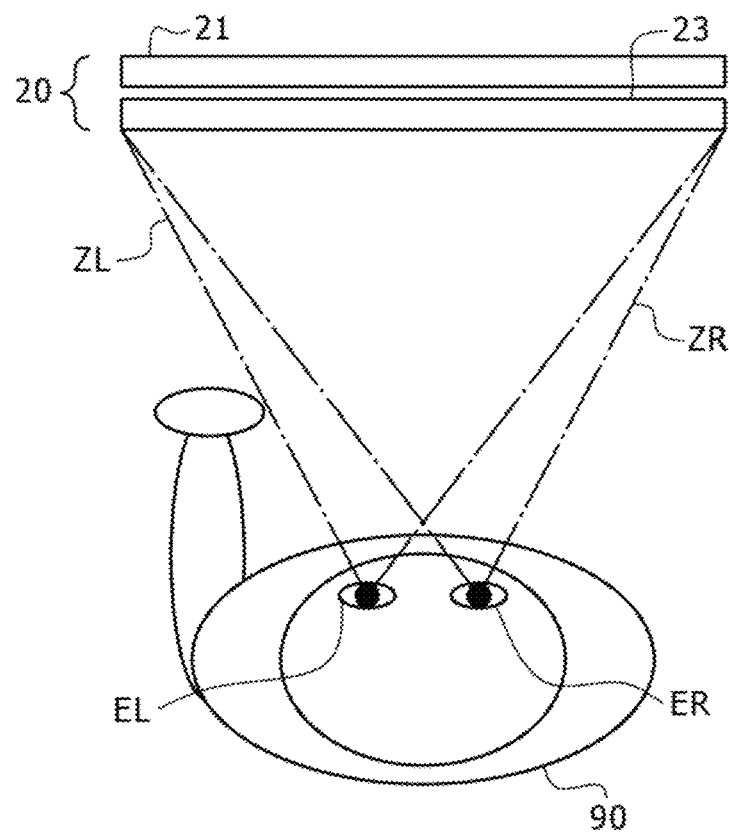
FIG. 2 is a schematic diagram illustrating a relation between an image display apparatus practiced as a second embodiment of the disclosure and an observer.

The following more specifically describes the present disclosure by use of the second embodiment thereof. Referring to FIG. 2, there is shown a schematic diagram illustrating a relation between a display apparatus practiced as the second embodiment of the present disclosure and an observer.

A 3D image display apparatus 20 is a display apparatus configured to display a 3D image that can be observantly viewed by an observer on the basis of binocular parallax. The 3D image display apparatus 20 has an LCD (Liquid Crystal Display) panel 21 and a lenticular lens 23. The LCD panel 21 displays a left-eye image and a right-eye image. The lenticular lens 23 refracts an incident light received from the LCD panel 21 to output the left-eye image displayed on the LCD panel 21 to a left-eye image observation zone ZL and the right-eye image displayed on the LCD panel 21 to a right-eye image observation zone ZR. Consequently, the 3D image display apparatus 20 allows the left-eye EL and the right-eye ER approximately 65 mm apart from each other of the observer 90 positioned at a predetermined distance from the viewing plane of the 3D image display apparatus 20 to have the left-eye image and the right-eye image respectively. The left-eye image and the right-eye image are images with a parallax set, so that the observer 90 can recognize the images displayed on the 3D image display apparatus 20 as a 3D image.

The parallax between a left-eye image and a right-eye image can be set by shifting the display position with the left-type image and the right-eye image by a predetermined pitch (or a predetermined number of pixels for example).

It should be noted that the 3D image display apparatus 20 has been described so far to be based on a lenticular scheme; however, it is also practicable to use any one of known 3D image display schemes, such as a spatial division scheme like a barrier scheme and a temporal division scheme based on shutter glasses.

Figure 3:
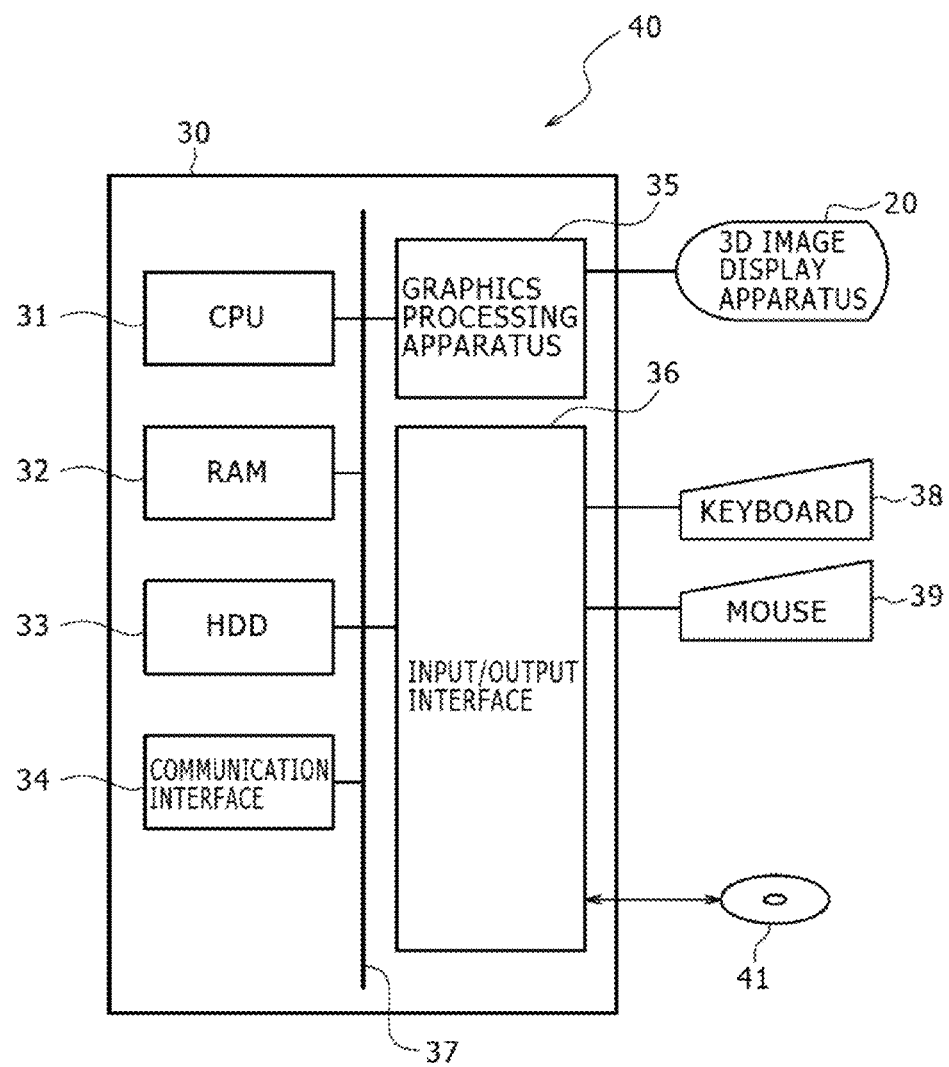
FIG. 3 is a block diagram illustrating an exemplary hardware configuration of the image display apparatus practiced as the second embodiment of the disclosure.

The following describes an exemplary hardware configuration of an image display apparatus. Referring to FIG. 3, there is shown an exemplary hardware configuration of an image display apparatus practiced as the second embodiment of the present disclosure. An image display apparatus 40 is configured by an information processing apparatus 30 configured to execute predetermined information processing including image processing and a 3D image display apparatus 20 configured to displayably output an image generated by the information processing apparatus 30 as a 3D image.

The information processing apparatus 30 is entirely controlled by a CPU (Central Processing Unit) 31. The CPU 31 is connected with a RAM (Random Access Memory) 32, a HDD (Hard Disk Drive) 33, a communication interface 34, a graphics processing apparatus 35, and an input/output interface 36 via a bus 37.

The RAM 32 temporarily stores at least a part of OS (Operating System) programs and application programs that are executed by the CPU 31. In addition, the RAM 32 stores various kinds of data that are required for the CPU 31 to execute various kinds of processing. The HDD 33 stores the OS programs and application programs.

The graphics processing apparatus 35 is connected with the 3D image display apparatus 20. The 3D image display apparatus 20 displays a predetermined GUI (Graphical User Interface) configured to allow a user to execute an information processing job. Under the control of the CPU 31, the graphics processing apparatus 35 displays an image on the 3D image display apparatus 20.

The input/output interface 36 is connected with a keyboard 38 and a mouse 39. In addition, the input/output interface 36 is connectable with a portable recording media interface configured to write information to a portable recording media 41 and read information from the portable recording media 41. The input/output interface 36 transmits signals supplied from the keyboard 38, the mouse 39, and the portable recording media interface to the CPU 31 via the bus 37.

The communication interface 34 is connected to a network, not shown. The communication interface 34 transmits and receives data with other computers via a network.

The hardware configuration described above realizes the processing functions of the second embodiment of the present disclosure.

It should be noted that the information processing apparatus 30 can be configured by including modules made up of an FPGA (Field Programmable Gate Array) and a DSP (Digital Signal Processor), for example, thereby excluding the CPU 31. If such a configuration is used, the information processing apparatus 30 has a nonvolatile memory (an EEPROM (Electrically Erasable and Programmable Read Only Memory), a flash memory, or a flash memory type memory card, for example), thereby storing the module firmware therein. The nonvolatile memory can store firmware via the portable recording media 41 or the communication interface 34. As described above, the information processing apparatus 30 can update firmware by rewriting the firmware stored in the nonvolatile memory.

Figure 4:
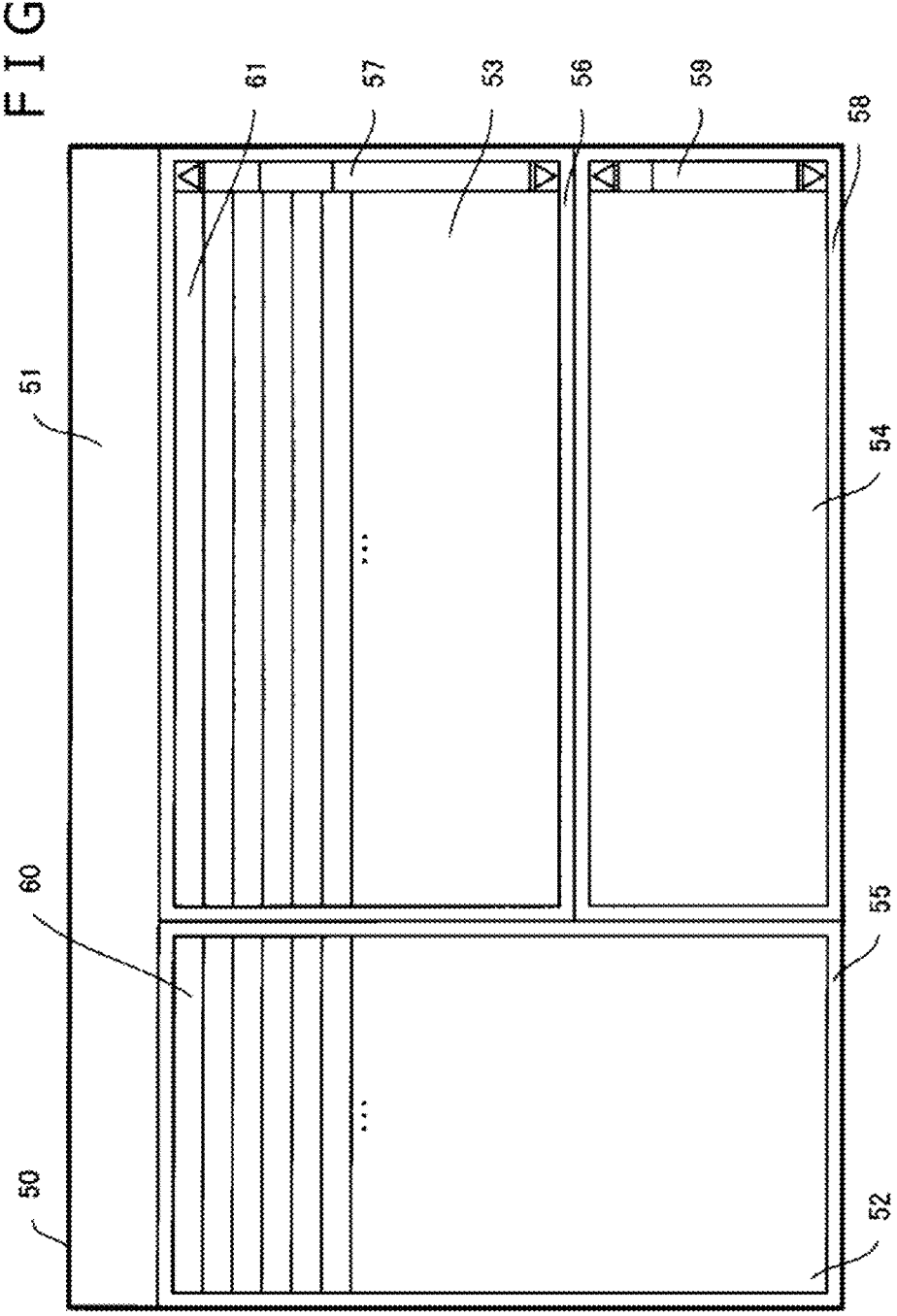
FIG. 4 is a diagram illustrating an exemplary display of a mailer practiced as the second embodiment of the disclosure.

The following describes a display screen of a mailer that is displayed by the 3D image display apparatus 20. Referring to FIG. 4, there is shown an exemplary display of a mailer practiced as the second embodiment of the present disclosure.

A mailer is an electronic email client configured to transmit/receive, browse, and manage electronic email and connected to an email server, not shown, via a network. A mailer is an application program that operates on the OS and displays to realize functions to be provided on a window 50.

The window 50 is configured by an operation display section 51, a folder display section 52, a list display section 53, and a preview display section 54. The operation display section 51 displays menus and icons for executing various operations as the mailer.

The folder display section 52 displays an in-box. For the in-box, folders (a root folder, sub holders, and so on) for storing received email messages in a tree structure. The folder display section 52 can display two or more folder display lines 60 inside a folder display section frame 55. The folder display section 52 displays one folder in one folder display line 60.

With the folder display section 52, a depth position in a 3D image display can be set for each folder display line 60 and a folder can be displayed by shifting the depth position in correspondence with a layer depth (or folder attribute information) in the folder tree structure.

The folder display section frame 55 (or a peripheral display section) is displayed at the same depth position as the folder display line 60 (or a display element) focused (or selected) in the folder display section 52, thereby allowing the user to easily understand a depth positional relation between the focused folder display line 60 and another folder display line 60. It should be noted that the folder display section frame 55 may be displayed on the viewing plane of the 3D image display apparatus 20 to allow the user to easily understand the depth positional relation between two or more folder display lines 60.

The list display block 53 displays a list of email messages stored in a folder selected in the folder display section 52. The list display block 53 can display two or more email display lines 61 inside a list display section frame 56. The list display block 53 displays one email message on one email display line 61. One email display line 61 can display two or more attributes, such as date of reception, title, sender, read/unread display, and importance display, for example.

With the list display block 53, the depth position in 3D image display can be set for each email display line 61, thereby displaying email messages with the depth positions differentiated corresponding to the predetermined attributes of the email messages (or email attribute information).

The list display section frame 56 (or the peripheral display section) is displayed at the same position as that of the email display line 61 focused in the list display block 53, thereby allowing the user to easily understand the depth positional relation between the focused email display line 61 and another email display line 61. It should be noted that the list display section frame 56 may be displayed on the viewing plane of the 3D image display apparatus 20 to allow the user to easily understand the depth positional relation between two or more email display lines 61.

The preview display section 54 displays an email message selected in the list display block 53, in a preview manner. The preview display section 54 can preview-display email messages inside a preview display section frame 58. With the preview display section 54, the depth position in email 3D image display can be set, thereby displaying email at the depth position corresponding to a predetermined attribute of email (or attribute information of email contents).

The preview display section frame 58 (or the periphery display section) is displayed on the viewing plane of the 3D image display apparatus 20 to allow the user to easily understand the depth positional relation of the email messages displayed in a preview manner.

It should be noted that, because the list display section frame 56 displays a list that cannot be fully displayed in the frame, the list display section frame 56 has a UI (User Interface) 57 that can select a display range (or a list to be displayed). In order to display email messages that cannot be all displayed in the frame, the preview display section frame 58 has a UI 59 that can select a display range. For the UI 57 and the UI 59, slide bars are shown for example; however, the UI 57 and the UI 59 may be shown in other manners. In the above-description, the folder display section 52 was shown with no UI displayed; if folders that cannot be fully displayed in the frame are to be displayed, the folder display section 52 displays a UI that selects a display range (or folders to be displayed).

Figure 5:
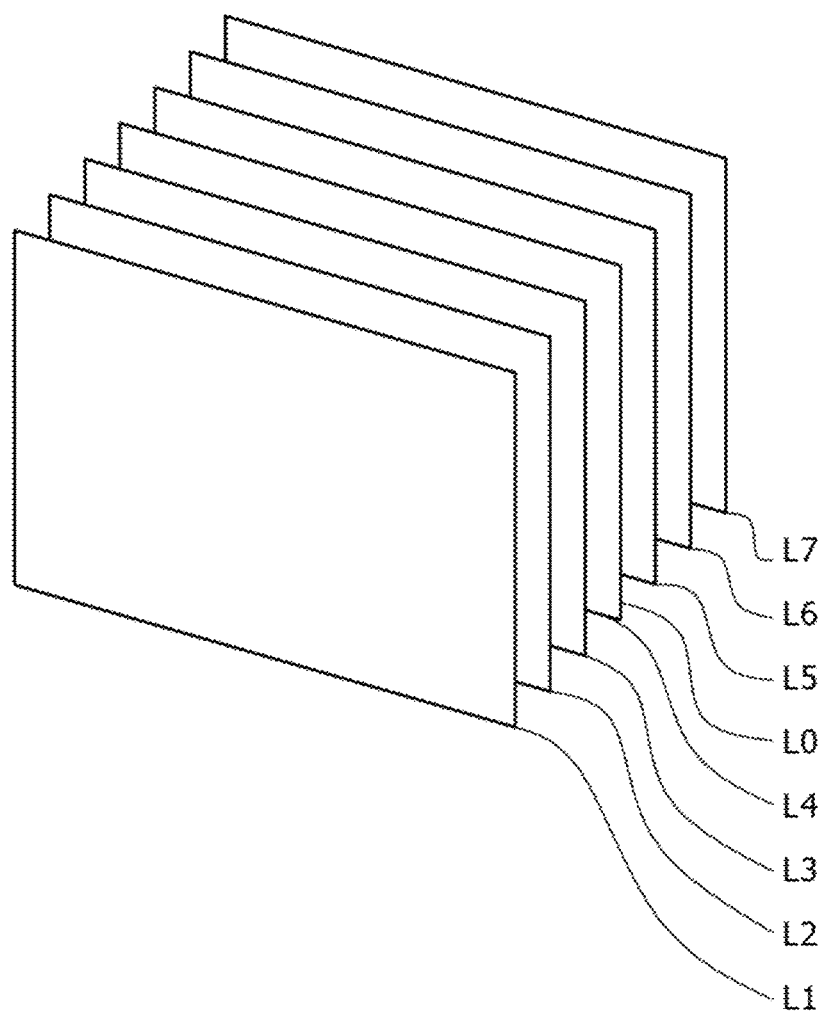
FIG. 5 is a diagram illustrating a concept of layers practiced as the second embodiment of the disclosure.

The following describes a mailer display screen that is displayed by the 3D image display apparatus 20. Referring to FIG. 5, there is shown a concept of layers practiced as the second embodiment of the present disclosure.

The information processing apparatus 30 virtually sets layers for each display unit in the depth direction set in the 3D image display apparatus 20. Two or more layers are set. In the second embodiment of the present disclosure, eight layers, L0, L1, L2, L3, L4, L5, L6, and L7 are set. In the layer L0, a display object for facilitating the understanding a depth position of an observer is set. For example, the operation display section 51, the folder display section frame 55, the list display section frame 56, the preview display section frame 58, the UI 57, and the UI 59 are set to the layer L0. To layer L1 through L7, display objects that can be displayed at different depth positions are set. For example, the folder display line 60 and the email display line 61 are set to layer L1 through L7. In this case, because there are seven layers, the information processing apparatus 30 can express the depths of seven steps.

Figures 6, 7:
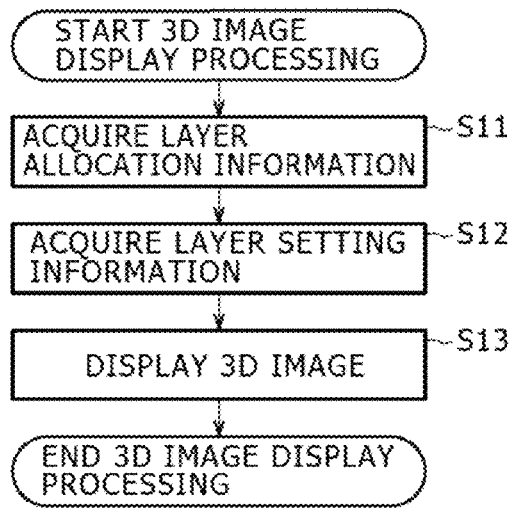
FIG. 6 is a flowchart indicative of 3D image display processing practiced as the second embodiment of the disclosure.
FIG. 7 is a diagram illustrating one example of layer allocation information practiced as the second embodiment of the disclosure.

The following describes 3D image display processing to be executed by the information processing apparatus 30 with reference to FIG. 6. FIG. 6 is a flowchart indicative of the 3D image display processing practiced as the second embodiment of the present disclosure.

[Step S11]

The information processing apparatus 30 acquires layer allocation information. Layer allocation information is indicative of a relation between a display object and a layer to which the display object is allocated

[Step S12]

The information processing apparatus 30 acquires layer setting information. Layer setting information is indicative of display contents of each layer.

[Step S13]

The information processing apparatus 30 executes 3D image display on the basis of the layer allocation information and the layer setting information. The information processing apparatus 30 divides the display objects into groups on the basis of the layer allocation information and identifies the display contents of each group on the basis of the layer setting information, thereby identifying the display contents for each display object.

As described above, by allocating display objects to layers, namely, by grouping display objects, the information processing apparatus 30 can facilitates the manipulation of display objects on a layer basis.

Figures 8, 9:
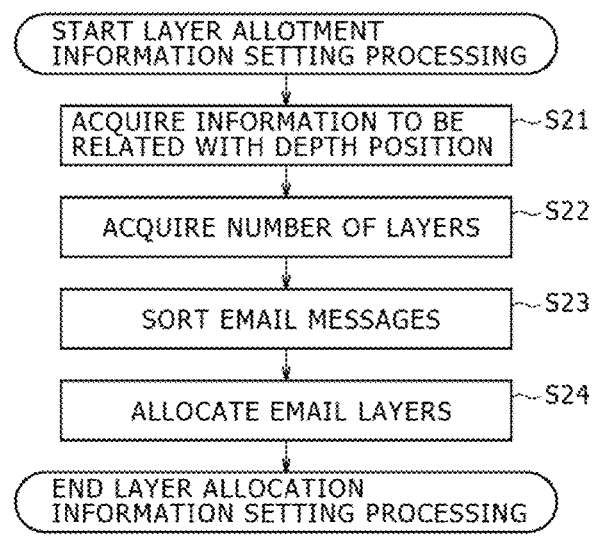
FIG. 8 is a diagram illustrating one example of layer setting information practiced as the second embodiment of the disclosure.
FIG. 9 is a flowchart indicative of layer allocation information setting processing practiced as the second embodiment of the disclosure.

The following describes details of layer allocation information and layer setting information with reference to FIG. 7 and FIG. 8. FIG. 7 shows one example of the layer allocation information practiced as the second embodiment of the present disclosure. FIG. 8 shows one example of the layer setting information practiced as the second embodiment of the present disclosure.

The layer allocation information 80 is indicative of a relation between an email display line and a layer to which the email display line is allocated. Email display lines "1" through "6" are allocated to layer L1 through L6, respectively, and email display lines "7" through "10" are allocated to layer L7. To be more specific, email display lines "1" through "10" are grouped to be allocated to layer L1 through layer L7. In addition, the layer allocation information 80 includes information indicative of relations between email display lines, corresponding message-ID (or identification information for uniquely identifying email messages), and attribute information of each email message (date of reception for example).

The layer setting information 81 sets a left-eye image correction value, a right-eye image correction value, a font size, and a blur effect of each layer. The left-eye and right-eye image correction values are correction values (namely, parallax amounts) in the left and the right directions, respectively, relative to a display object displaying position. The font size is the size of a font with which a display object is displayed in a text. The font size is set so as to be smaller as the depth position gets deeper and larger as the depth position gets shallower. The blur effect is the value of setting a blur effect to be added to a display object ("0"=no blur, "1"=low blur, "2"=middle blur, and "3"=high blur). The blur effect is set so as to be lower as the depth position gets deeper and higher as the depth position gets shallower. The setting of the font size and the blur effect contributes to aid the user recognize a 3D image.

According to the layer setting information 81, layer L0 has no parallax because the left-eye image correction value and the right-eye image correction value are both "0" and the display object allocated to layer L0 is displayed on the viewing plane (namely, in two-dimensional (2D) manner). With layer 1, the left-eye image correction value is "−3" and the right-eye image correction value is "3," so that the display object allocated to layer L1 is displayed in the depth direction from the viewing plane. With layer 2, the left-eye image correction value is "−2" and the right-eye image correction value is "2," so that the display object allocated to layer L2 is displayed in the depth direction from the viewing plane. With layer 3, the left-eye image correction value is "−1" and the right-eye image correction value is "1," so that the display object allocated to layer L3 is displayed in the depth direction from the viewing plane. With layer 4, the left-eye image correction value is "0" and the right-eye image correction value is "0," so that the display object allocated to layer L4 is displayed on the viewing plane. With layer L5, the left-eye image correction value is "1" and the right-eye image correction value is "−1," so that the display object allocated to layer L5 is displayed in the forward direction from the viewing plane. With layer L6, the left-eye image correction value is "2" and the right-eye image correction value is "−2," so that the display object allocated to layer L6 is displayed in the forward direction from the viewing plane. With layer L7, the left-eye image correction value is "3" and the right-eye image correction value is "−3," so that the display object allocated to layer L7 is displayed in the forward direction from the viewing plane. Consequently, with layers L1 through L7, seven steps of depth positions are set with the viewing plane between the depth direction and the forward direction. It should be noted that, with layer L4, the depth position is set on the same viewing plane as that of layer L0.

The following describes layer allocation information setting processing that is executed by the information processing apparatus 30 with reference to FIG. 9. FIG. 9 is a flowchart indicative of the layer allocation information setting processing practiced as the second embodiment of the present disclosure. The layer allocation information setting processing allocates email messages to be displayed to layers. The layer allocation information setting processing is executed before the 3D image display processing.

[Step S21]

The information processing apparatus 30 acquires information to be associated with a depth position. The information to be associated with a depth position is attribute information of each email message. For example, the layer allocation information 80 uses date of reception as the information to be associated with a depth position.

[Step S22]

The information processing apparatus 30 acquires the number of layers. The number of layers may be set as desired and changeable depending on an operation done to the mailer or an object to be displayed. For example, the number of layers may be 5 in the case of folder operation and 7 in the case of an email operation. Further, the number of layers may be 5 if the number of email messages to be displayed is below 10 and 7 if the number of email messages to be displayed is 10 or higher, for example.

[Step S23]

The information processing apparatus 30 sorts email messages on the basis of the information associated with depth. For example, the layer allocation information 80 sorts message-IDs by date of reception (in the ascending order for example).

[Step S24]

The information processing apparatus 30 executes email layer allocation. For example, the layer allocation information 80 allocates the sorted message-IDs from layer L1 to layer L7.

As described above, the information processing apparatus 30 executes the layer allocation based on the information associated with depth.

Figures 10, 11:
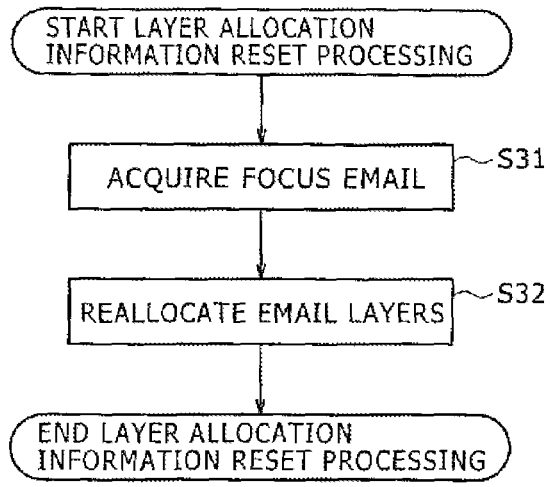
FIG. 10 is a flowchart indicative of layer allocation information resetting processing practiced as the second embodiment of the disclosure.
FIG. 11 is a diagram illustrating one example of layer allocation information obtained after the reallocation practiced as the second embodiment of the disclosure.

The following describes layer allocation information resetting processing that is executed by the information processing apparatus 30 with reference to FIG. 10 and FIG. 11. FIG. 10 is a flowchart indicative of layer allocation information resetting processing practiced as the second embodiment of the present disclosure. FIG. 11 shows one example of layer allocation information obtained after the reallocation of the second embodiment of the present disclosure. The layer allocation information resetting processing reallocates email messages to be displayed to layers. The layer allocation information resetting processing is executed before the 3D image display processing.

[Step S31]

The information processing apparatus 30 acquires a focused email message (or an email message selected by an operation on the mouse 39 for example).

[Step S32]

The information processing apparatus 30 executes the email layer reallocation with reference to the focused email message.

For example, assumed that the information processing apparatus 30 acquire email message message-ID "Midxxx6" in the layer allocation information 80 as the focused email message. Email message having message-ID "Midxxx6" in the layer allocation information 80 is allocated to layer "6." At this moment, because email messages having message-IDs "Midxxx7" to "Midxxx10" have both been allocated to layer "7," it is not easy for the user to understand the early-late relation despite the proximity to the email message having message-ID "Midxxx6."

It should be noted here that the result of the email layer reallocation is indicative of layer allocation information 82. In the layer allocation information 82, the email message having message-ID "Midxxx6" is allocated to layer "4." At this moment, the email messages having message-IDs "Midxxx4" to "Midxxx8" are allocated to layer "2" to layer "6" respectively, so that the early-late relation of the email message having message-ID "Midxxx6" is easy to understand.

The information processing apparatus 30 can execute the 3D image display processing after the email layer reallocation processing to switch the email depth position from the state before the layer reallocation to the state after the layer reallocation. It should be noted that, in the description so far, the layer reallocation that is executed with the updating of a focused email message being the trigger; however, it is also practicable for the information processing apparatus 30 to use such operation inputs as the trigger of layer reallocation as email sort, move, and delete, for example.

Consequently, the information processing apparatus 30 can provide an email handling environment that is easier to see and operate in the 3D image display apparatus 20, thereby enhancing the user processing efficiency.

It should be noted that, if the order (up-down direction) to be displayed on the email display line 61 of the email messages to be read is sorted by attribute information (title and sender for example) other than reception date, the arrival relation of reception dates can easily be understood from the depth relation. Further, because the layer reallocation of email messages is executed with reference to the focused email message, the early-late relation of reception dates can be easily understood from the depth relation even if the email messages have not been sorted in the up-down direction. In addition, by setting the depth position of the layer of the focused email and the depth position of the layer of the list display section frame 56 to the same position, the early-late relation of reception dates can be understood more easily.

It should also be noted that, in order to easily understand newly arrived email messages, the information processing apparatus 30 may execute email layer reallocation such that the most recent email message comes to the front-most position. In this case, the information processing apparatus 30 may execute reallocation such that the least-recent email message is placed at the most rear position and other email messages are place between the most-recent email message and the least-recent email message in a proper depth positions.

The Third Embodiment

The following describes the third embodiment of the present disclosure for facilitating the understanding of the contents of email. The third embodiment of the present disclosure differs from the second embodiment of the present disclosure in that the contents of email are displayed. It should be noted that, with the description of the third embodiment, configurations similar to those previously described with reference to the second embodiment are denoted by the same reference symbols and the description thereof will be skipped.

Figure 12:
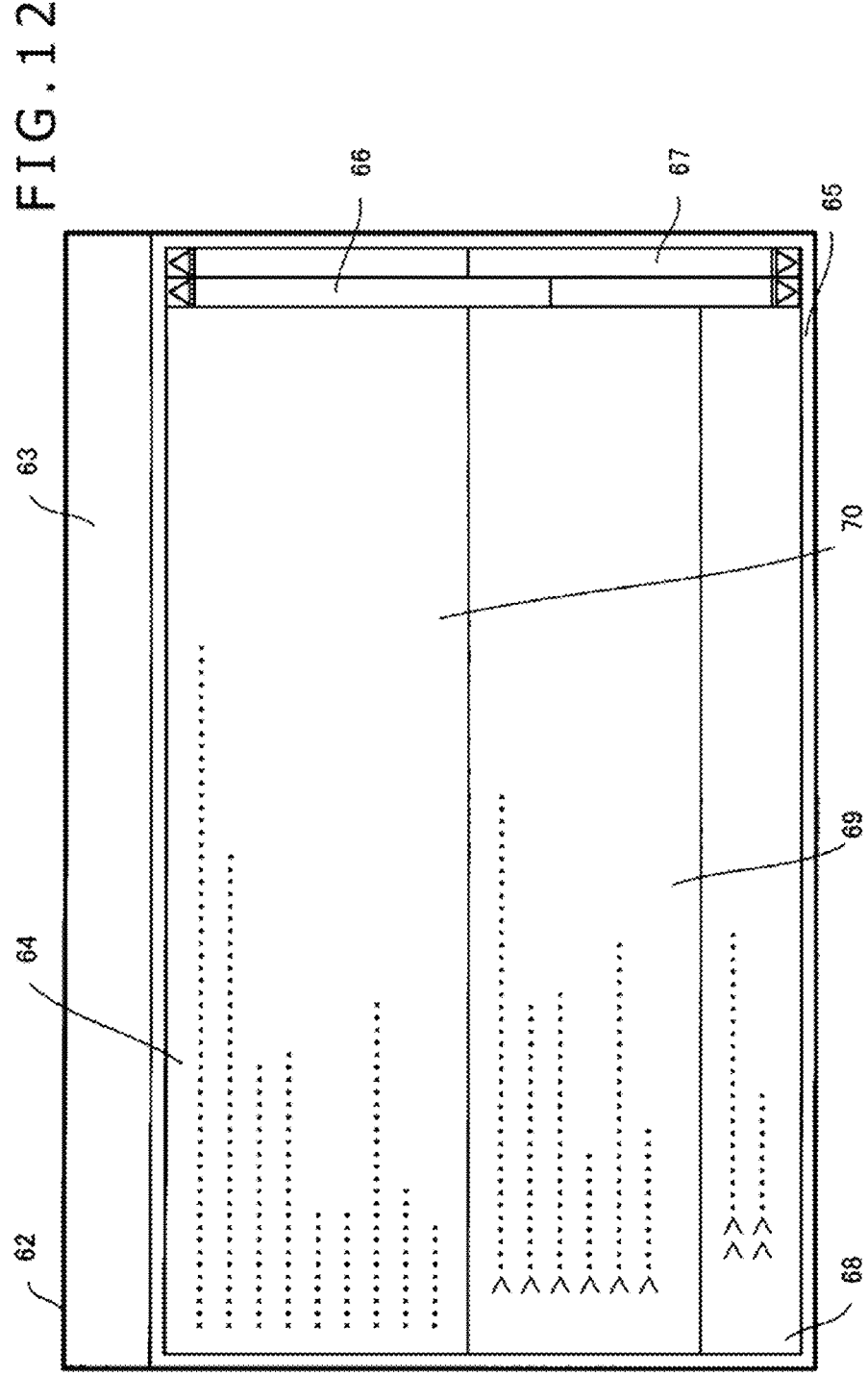
FIG. 12 is a diagram illustrating an exemplary display a mailer practiced as a third embodiment of the disclosure.

First, a display screen of a mailer to be displayed by a 3D image display apparatus 20 will be described. Referring to FIG. 12, there is shown a display example of a mailer practiced as the third embodiment of the present disclosure. The mailer practiced as the third embodiment displays an email browsing window 62.

The email browsing window 62 is configured by a head information display section 63, an email display section 64, and an email display section frame 65. The header information display section 63 displays the header information of each email message. The email display section 64 displays the contents of each email message. The email display section 64 divides the contents of email messages by quote depth and arranges the divided email contents to two or more divided areas 68, 69, and 70. It should be noted that the number of divided areas may be less or more than three.

For example, an email message may be added to a received email message, thereby repeating sending and receiving two or more times. In such a situation, it may be difficult to understand the temporal relation of communication, such as understanding where the most recent return email message is. In addition, if an original text and a text added thereto are not in proximity to each other, it is difficult, after reading one, to search for the display position of the other.

In order to solve the above-mentioned problem, the mailer identifies the quote depth (or the update count) by the number of symbols ">" attached to preceding lines to divide the contents of an email message. The divided area 70 is an area with the number of symbols ">" attached to the preceding lines being 0. The divided area 69 is an area with the number of symbols ">" being 1. The divided area 68 is an area with the number of symbols ">" being 2. It should be noted that the division of email contents is not limited to that described above. The email contents may be divided by any other rules.

The email display section frame 65 has a UI 66 that allows the selection of a display range (the email contents to be displayed) in order to display the email contents that cannot be fully displayed in that frame. In addition, the email display section frame 65 has a UI 67 that allows the selection of a display range on a divided area basis. The UI 67 provides a high-speed switching to a desired display range, thereby enhancing user operation efficiency.

The following describes divided area 3D image display processing to be executed by the information processing apparatus 30 with reference to FIG. 13. FIG. 13 is a flowchart indicative of the divided area 3D image display processing practiced as the third embodiment of the present disclosure. The divided area 3D image display processing divides the email contents to be displayed and allocates the divided email contents to the layers of divided areas. The divided area 3D image display processing is executed before the 3D image display processing.

[Step S41]

The information processing apparatus 30 divides email contents by quote depth.

[Step S42]

The information processing apparatus 30 executes the layer allocation of divided areas. To be more specific, the information processing apparatus 30 generates layer allocation information.

[Step S43]

The information processing apparatus 30 generates layer setting information.

As described above, the information processing apparatus 30 can set a depth position for each quote depth to display email contents.

Figures 15, 16:
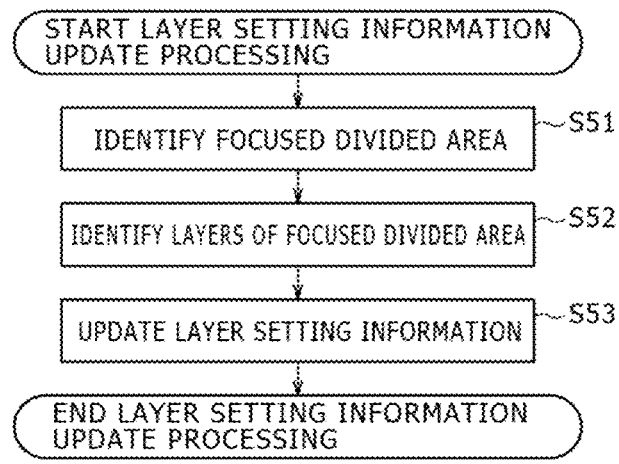
FIG. 15 is a diagram illustrating one example of layer setting information practiced as the third embodiment of the disclosure.
FIG. 16 is a flowchart indicative of layer setting information update processing practiced as the third embodiment of the disclosure.

The following describes specific examples of the layer allocation information and the layer setting information practiced as the third embodiment of the present disclosure with reference to FIG. 14 and FIG. 15. FIG. 14 shows one example of the layer allocation information practiced as the third embodiment of the present disclosure. FIG. 15 shows one example of the layer setting information practiced as the third embodiment of the present disclosure.

The layer allocation information 83 is information indicative of the relation between an area ID and a layer to which the area ID is allocated. Area IDs "area idxxx1" through "area idxxx5" are allocated to layer L1 through layer L5, respectively. The area ID is identification information that can uniquely identify an divided area. It should be noted that, if the number of area IDs is large or there are area IDs that are not displayed at the same time because of the lack of proximity, two or more grouped divided IDs may be allocated to layers as required.

The layer setting information 84 sets a left-eye image correction value, a right-eye image correction value, a font size, and a blur effect of each layer.

According to the layer setting information 84, layer L1 has no parallax because the left-eye image correction value and the right-eye image correction value are both "0" and a display object allocated to layer L1 is displayed on the viewing plane (namely, in 2D display). With layer L2, the left-eye image correction value is "−1" and the right-eye image correction value is "1," so that a display object allocated to layer L2 is displayed in the depth direction backward from the viewing plane. With each of layer L3 through layer L5, the left-eye image correction value is "−2" and the right-eye image correction value is "2," so that a display object allocated to each of layer L3 through layer L5 is displayed in the depth direction backward from layer L2. Consequently, for layer L1 through layer L5, three steps of depth positions are set from the depth direction to the viewing plane.

An email display section frame 65 is allocated to layer L0. For layer L0, the depth position is set to the same viewing plane as that of layer L1 in order to explicitly show a focused divided area (a divided area selected by the operation of a mouse 39 for example). The selection of a focus area is changeable by operating the UI 67 that is a slide bar.

The divided area of area ID "area idxxx1" of the email contents displayed in accordance with the layer allocation information 83 and the layer setting information 84 is displayed on the viewing plane that is the front-most plane and the other divided areas are sequentially displayed in the depth direction. Thus, two or more divided areas are displayed in different depth positions, so that the user can easily understand the divided areas.

The following describes layer setting information update processing to be executed by the information processing apparatus 30 with reference to FIG. 16 and FIG. 17. FIG. 16 is a flowchart indicative of the layer setting information update processing practiced as the third embodiment of the present disclosure. FIG. 17 shows one example of the layer setting information practiced as the third embodiment of the present disclosure after resetting. The layer setting information update processing updates layer setting information in order to update a depth position that becomes necessary as a result of the focusing of a divided area. The layer setting information update processing is executed before the 3D image display processing.

[Step S51]

The information processing apparatus 30 identifies the area ID of a focused divided area.

[Step S52]

The information processing apparatus 30 references the layer allocation information to identify the layer corresponding to the identified area ID.

[Step S53]

The information processing apparatus 30 updates the layer setting information such that the layer corresponding to the identified area ID is positioned on the viewing plane.

For example, if the information processing apparatus 30 identifies area ID "area idxxx2" as the area ID of a focused divided area, then the information processing apparatus 30 can reference the layer allocation information 83 to identify layer L2 from area ID "area idxxx2." The information processing apparatus 30 also updates the setting information of the other layers in order for layer L2 to be displayed on the viewing plane. Thus, the information processing apparatus 30 updates the layer setting information 84 to layer setting information 85.

Consequently, if the focusing of divided areas is changed, the information processing apparatus 30 facilitates the user understanding of divided areas, thereby enhancing the user processing efficiency.

It should be noted that, in the above-mentioned configuration, two or more divided areas are arranged in the depth direction with the order of quote depth (layer) fixed; however, it is also practicable to arrange a focused divided area at the front-most viewing plane.

It should also be noted that the divided area that provides the front-most viewing plane may be displayed forward from the viewing plane.

The email contents divided as described above can be displayed at different depth positions for different divided areas, thereby facilitating the understanding of a positional relation between divided areas.

In the above-mentioned configuration, the division of email contents is executed by quote depth; however, it is also practicable to divide email contents by another reference. For example, in the case of HTML (HyperText Markup Language) email messages, the email contents may be divided into areas by use of HTML tags as delimiters. This method allows the displaying of a hyperlink or an image for example at a depth position different from that of an email body text and, at the same time, allows the user to access email messages at high speeds through the UI 67.

In addition, the division of email contents may be executed by use of a given character string including an escape sequence in addition to a head line tab or space for example. This method allows the displaying an email body text at different depth positions on a text or paragraph basis.

The Fourth Embodiment

Figure 18:
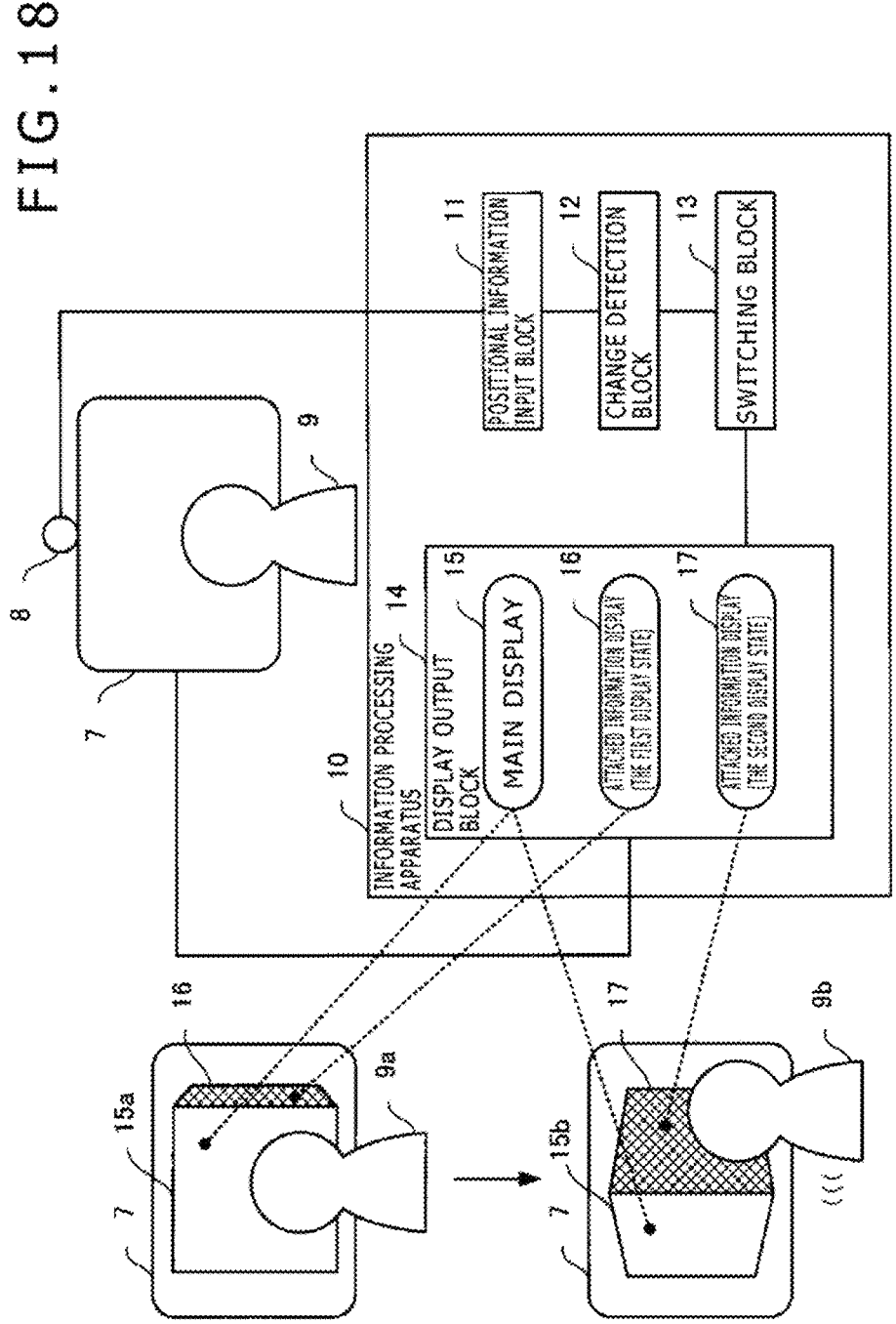
FIG. 18 is a schematic diagram illustrating an exemplary configuration of an information processing apparatus practiced as a fourth embodiment of the disclosure.

The following describes an exemplary configuration of an information processing apparatus practiced as the fourth embodiment of the present disclosure with reference to FIG. 18. FIG. 18 shows an exemplary configuration of the information processing apparatus practiced as the fourth embodiment of the present disclosure.

An information processing apparatus 10 generates display contents to be displayed on a display apparatus 7 and outputs the generated display contents to the display apparatus 7 that is a 3D image display apparatus configured to display a 3D image that can be viewed by an observer on the basis of binocular parallax. The information processing apparatus 10 detects a position of an observer 9 from an image in which the observer 9 is taken by an imaging apparatus 8. The information processing apparatus 10 updates the display contents to be displayed on the display apparatus 7 in accordance with the position of the observer 9.

The information processing apparatus 10 has a positional information input block 11, a change detection block 12, a switching block 13, and a display output block 14.

The display output block 14 outputs main display 15 and attached information displays 16 and 17 that display attached information associated with the main display 15 to the display apparatus 7. The main display 15 is mainly presented to the observer 9. To be more specific, the main display 15 is mainly presented to the observer 9 by use of a display object to be arranged in a virtual space (or a virtual 3D space). The attached information displays 16 and 17 are presented to the observer 9 as the attached information associated with the main display 15, namely, in subordinate to the main display 15. The attached information displays 16 and 17 are presented to the observer 9 in subordinate to the main display 15 by use of a display object arranged in a virtual space.

The attached information display 16 is an attached information display of a first display state. The attached information display 17 is an attached information display of a second display state that is easier for an observer to make observation than the first display state. As compared with the attached information display 16, the attached information display 17 provides an easy-to-observe display state by any one of or a combination of enlargement of display area, change of display directions, and change of brightness, for example. It should be noted that the display states of the attached information display 16 includes a non-display state.

The positional information input block 11 enters positional information of the observer 9 who observes the display apparatus 7. Positional information identifies a position of the observer 9 on the basis of an image taken by the imaging apparatus 8. The imaging apparatus 8 is based on a CCD (Charge Coupled Device) image sensor or a CMOS (Complementary Metal Oxide Semiconductor) image sensor, for example.

The change detection block 12 detects a change in positional information. For example, the change detection block 12 compares positional information of an observer 9a at a first position with positional information of an observer 9b at a second position, thereby detecting whether there is a change in the positional information of the observer 9.

On the basis of the detection of a change in the positional information of the observer 9, the switching block 13 switches a display state of attached information display from the first display state to the second display state that is easier for the observer to make observation than the first display state.

For example, the information processing apparatus 10 executes an output operation to the display apparatus 7 such that a main display 15a is displayed to the front of a window display formed by a cuboid and the attached information display 16 to one side thereof for the observer 9a. If the positional information input block 11 enters the positional information of the observer 9b and the change detection block 12 detects a positional change from the observer 9a to the observer 9b, then the switching block 13 switches the attached information display 16 to be outputted by the display output block 14 to the attached information display 17. Namely, the information processing apparatus 10 executes an output operation to the display apparatus 7 such that the attached information display 17 is displayed to the front of the window display formed by a cuboid and the main display 15b to one side thereof for the observer 9b.

As described above, the information processing apparatus 10 can detect a positional change of the observer 9 to switch the attached information display 16 to the attached information display 17. Consequently, the observer 9 who observes the display apparatus 7 can easily switch between the display contents by a positional change of the observer 9, thereby enhancing the efficiency of the processing by the observer 9 (or the user).

Further, because the information processing apparatus 10 detects a positional change of the observer 9 to switch between the display contents of the display apparatus 7 that is a 3D image display apparatus, the information processing apparatus 10 can provide an operation that is easy for the observer 9 to acquire.

The Fifth Embodiment

The following describes the fifth embodiment of the present disclosure that is a more specific version of the fourth embodiment of the present disclosure. It should be noted that, with the description of the fifth embodiment, configurations similar to those previously described with reference to the second embodiment are denoted by the same reference symbols and the description thereof will be skipped.

Figure 19:
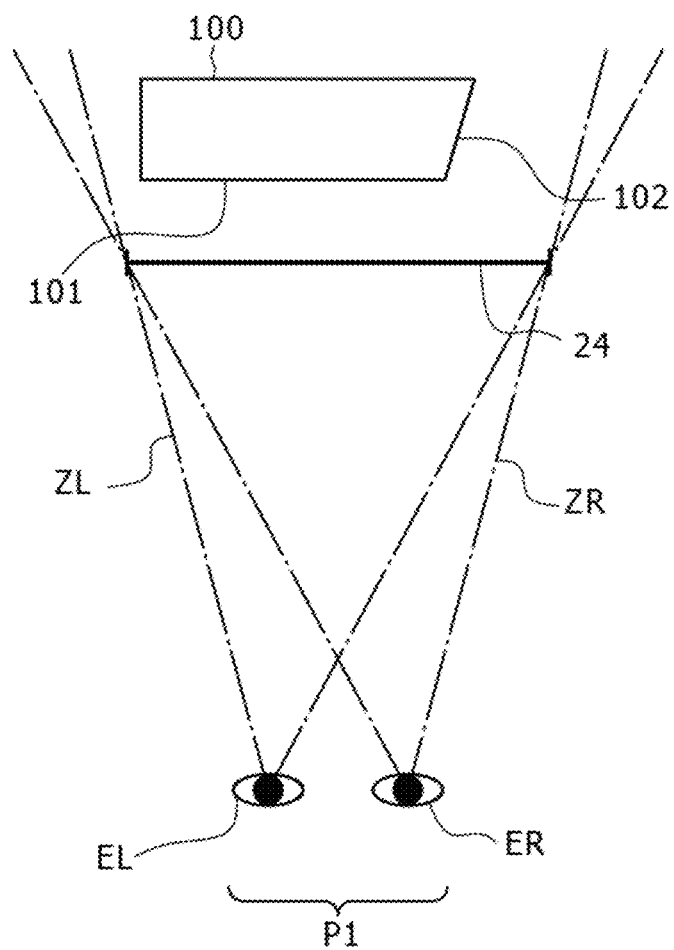
FIG. 19 is a schematic diagram illustrating a relation between a display object and an observer directly with a display screen directly confronted, practiced as a fifth embodiment of the disclosure.
Figure 20:
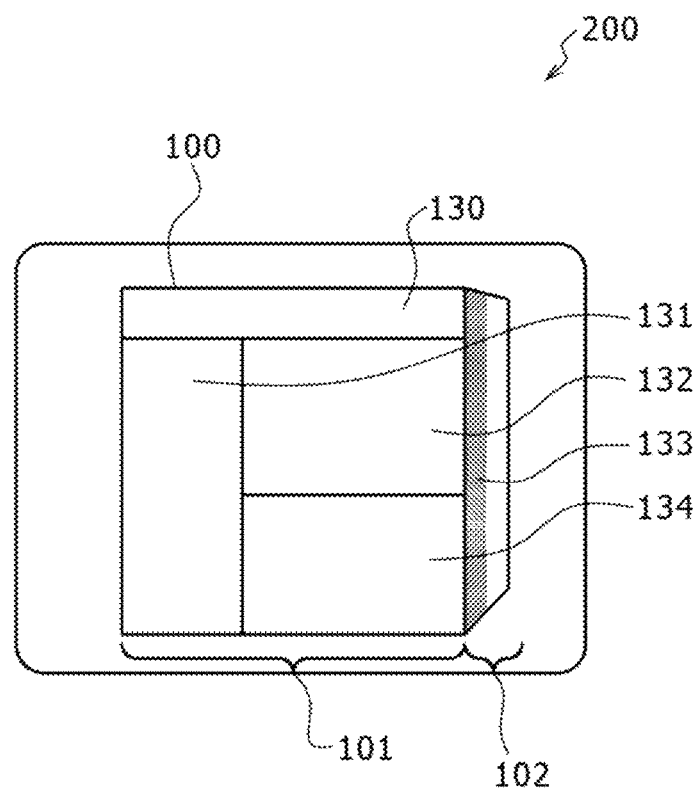
FIG. 20 is a schematic diagram illustrating an exemplary image display obtained with a display screen directly confronted, practiced as the fifth embodiment of the disclosure.
Figure 21:
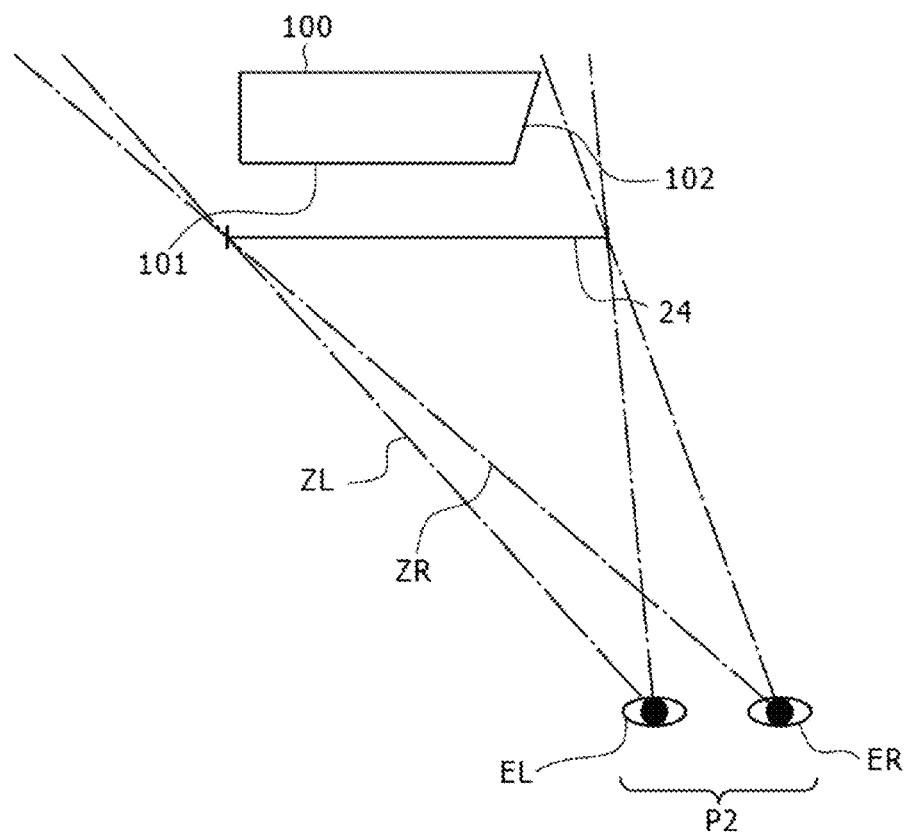
FIG. 21 is a schematic diagram illustrating a relation between a display object and an observer with a display screen not directly confronted, practiced as the fifth embodiment of the disclosure.
Figure 22:
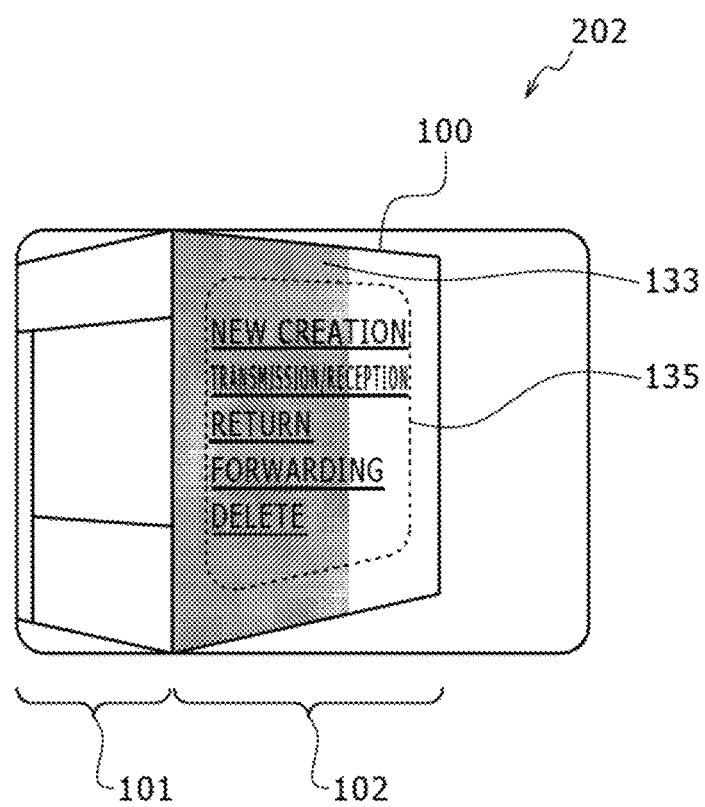
FIG. 22 is a schematic diagram illustrating an exemplary image display with a display screen not directly confronted, practiced as the filth embodiment of the disclosure.

First, a display object to be displayed by a 3D image display apparatus will be described by use of image display examples viewing plane directly confronting and viewing plane not directly confronting with reference to FIG. 19 through FIG. 22. FIG. 19 shows a relation between a display object and an observer at the time of viewing plane directly confronting practiced as the fifth embodiment of the present disclosure. FIG. 20 shows an image display example at the time of viewing plane directly confronting practiced as the fifth embodiment. FIG. 21 shows a relation between a display object and an observer at the time of viewing plane not directly confronting practiced as the fifth embodiment. FIG. 22 shows an image display example at the time of viewing plane not directly confronting practiced as the fifth embodiment.

In the fifth embodiment, on the basis that a right-eye image and a left-eye image are displayed on a viewing plane 24 of the 3D image display apparatus 20, images that appear (or that can be observantly viewed as 3D images by an observer 90) in the virtual space formed in the depth direction and the front direction of the viewing plane 24 are called as display objects. When left eye EL and right eye ER of the observer 90 are at observation point P1, namely, when left eye EL is at left-eye image observation zone ZL and right eye ER is at right-eye image observation zone ZR, the observer 90 can observantly view a display object 100 as a 3D image.

The display object 100 is set as a polyhedron having a main viewing plane 101 and an attached information viewing plane 102. The display object 100 is a display unit in which predetermined information is displayed, which is a window or an icon, for example.

The main viewing plane 101 of the display object 100 is the main viewing plane on which the display object 100 is displayed and the attached information viewing plane 102 is a viewing plane for displaying information attached to the main display and subordinate to the main viewing plane. The main viewing plane 101 shown in FIG. 20 is at a position easily observable by the observer 90 at observation position P1 as compared with the attached information viewing plane 102. The main viewing plane 101 is positioned directly confronting the observer 90 at observation point P1. The main viewing plane 101 displays an operation display section 130, a folder display section 131, a list display section 132, and a preview display section 134 of a mailer.

An image display example 200 is an image obtained by observing the display object 100 arranged in the virtual space from observation position P1. The display object 100 shown in the image display example 200 is a window of a mailer, in which the main viewing plane 101 is displayed as directing confronting the front and the attached information viewing plane 102 is displayed on one of the sides. The display object 100 is a trapezoid when looked down upon in the virtual space and the observer 90 at observation point P1 can confirm the attached information viewing plane 102. The attached information viewing plane 102 that is observable along with the main viewing plane 101 gives the observer 90 at observation point P1 the motivation of changing observation points.

The attached information viewing plane 102 displays a capacity display section 133. The capacity display section 133 displays a current capacity of the email that can be handled by the mailer to the upper limit of the capacity. The capacity display section 133 displays the current capacity by the ratio of a colored section occupying the attached information viewing plane 102. It should be noted that the upper limit of the capacity of email that can be handled by the mailer may be a mailer limit or an email server limit.

Observation point P2 shown in FIG. 21 is positioned to the right from observation point P1. The main viewing plane 101 is at a position shifted from the position of directly confronting the observer 90 at observation point P2. On the basis of the detection of a positional change from observation point P1 of the observer 90 to observation point P2, the 3D image display apparatus 20 switches between images to be displayed on the viewing plane 24 as shown in the image display example 202 shown in FIG. 22. Also, at observation point P2, a lenticular lens 23 refracts an incident light from an LCD 21, thereby outputting a left-eye image displayed by the LCD 21 to left-eye image observation zone ZL and a right-eye image displayed by the LCD panel 21 to right-eye image observation zone ZR.

The image display example 202 shown in FIG. 22 is an image obtained by observing the display object 100 arranged in the virtual space from observation point P2. The attached information viewing plane 102 of the display object 100 shown in the image display example 202 is larger in display area than the attached information viewing plane 102 shown in the image display example 200.

The enlarged attached information viewing plane 102 displays an operation display section 135 in addition to the capacity display section 133. The operation display section 135 displays an operation menu (newly create, transmit/receive, return, transfer, and delete for example) in the mailer. Consequently, the observer 90 can easily observe the capacity display section 133 and the operation display section 135 displayed on the attached information viewing plane 102.

It should be noted that the enlargement of the display area of the attached information viewing plane 102 can be realized by switching between virtual viewpoints at which the display object 100 is observed. In addition, this enlargement can be realized by switching between the orientations, sizes, or shapes of the display object 100 or a combination thereof.

Figure 23:
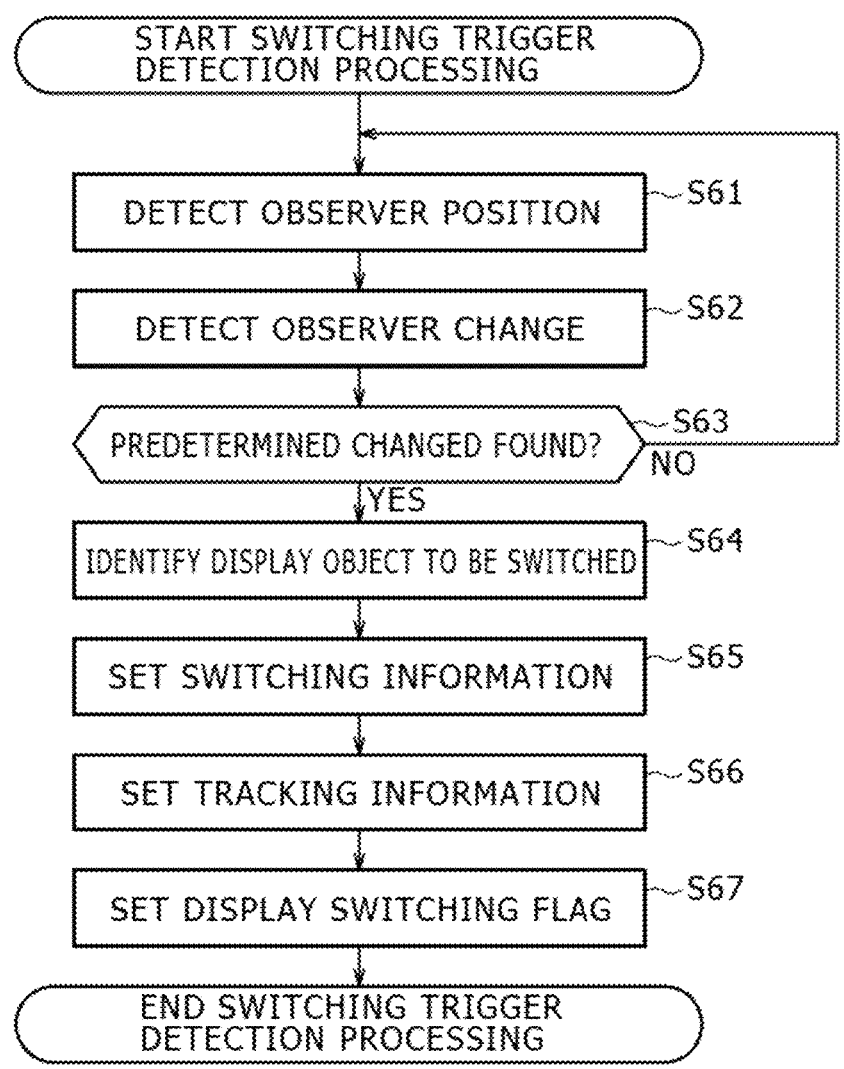
FIG. 23 is a flowchart indicative of switching trigger detection processing practiced as the fifth embodiment of the disclosure.

The following describes switching trigger detection processing to be executed by the information processing apparatus 30 with reference to FIG. 23 and FIG. 24. FIG. 23 is a flowchart indicative of the switching trigger detection processing practiced as the fifth embodiment of the present disclosure. FIG. 24 shows one example of switching information of the fifth embodiment of the present disclosure. The information processing apparatus 30 executes the switching trigger detection processing concurrently with the execution of a predetermined application. The switching trigger detection processing executes tracking of the observer 90 to determine a display switching timing and the setting of switching contents.

[Step S61]

The information processing apparatus 30 executes the positional detection of the observer 90 on the basis of the input from an imaging apparatus 22 (to be described later).

[Step S62]

The information processing apparatus 30 detects a predetermined change in the position of the observer 90.

[Step S63]

If a predetermined change has been detected in the position of the observer 90, the information processing apparatus 30 proceeds the process to step S64; otherwise, the information processing apparatus 30 proceeds the process to step S61.

[Step S64]

The information processing apparatus 30 identifies a display object to be switched for display. It should be noted that a display object to be switched for display may be more than one; for example, two or more display objects may be identified. A display object to be switched for display may be limited to one that satisfies a predetermined condition, such as an active window, for example.

[Step S65]

The information processing apparatus 30 sets switching information for each display object identified as a display switching object. Switching information 300 is one example of switching information that is set by the information processing apparatus 30. The switching information 300 is information for determining to which display mode a display object is to be switched. The switching information 300 includes identification information ("001" for example) for uniquely identifying a display object. In addition, the switching information 300 includes information ("thick width window" for example) that can identify the shape of a display object. Further, the switching information 300 includes information ("middle" for example) that can identify the size of a display object. The switching information 300 includes information ("x1, y1 and z1" for example) that can identify the position of a display object. The switching information 300 includes information ("dx1, dy1 and dz1" for example) that can identify the orientation of a display object. It should be noted that each of the above-mentioned pieces of information may be information that defines a specific value or an index for referencing predefined information, for example.

The switching information 300 includes display contents for each area set to a display object. For example, a display object identified by identification information "001" has display areas from area a to area f. "Operation display" (the main viewing plane) is set to area a, "folder display" is set to area b, "list display" is set to area c, "preview display" is set to area d, "capacity display" is set to area e, and "operation display (the main view plane" is set to area f. It should be noted that the area set to a display object may set to each face of a polyhedron display object, two or more areas obtained by dividing one plane, or a combination thereof.

[Step S66]

The information processing apparatus 30 sets tracking information. Tracking information is information associated with an observation position of the observer 90.

[Step S67]

The information processing apparatus 30 sets a display switching flag that provides display switching trigger and terminates the switching trigger detection processing.

It should be noted that a predetermined change to be detected in step S62 may be a predetermined movement (65 mm in the right direction (distance between left and right eyes), for example) in a predetermined direction of a tracking part (head, left eye EL, or right eye RE, for example).

A predetermined change to be detected in step S62 may be a predetermined inclination of the head (including face, left eye EL and right eye ER). In addition, a predetermined change to be detected in step S62 may be a predetermined rotation of the head (including face, left-eye EL and right eye ER, for example). Further, a predetermined change to be detected in step S62 may be a sight line direction detected from left eye EL and left pupil or right eye ER and right pupil. This configuration allows display switching without involving a large movement in the trunk of body, thereby further enhancing the efficiency of user processing.

Figure 25:
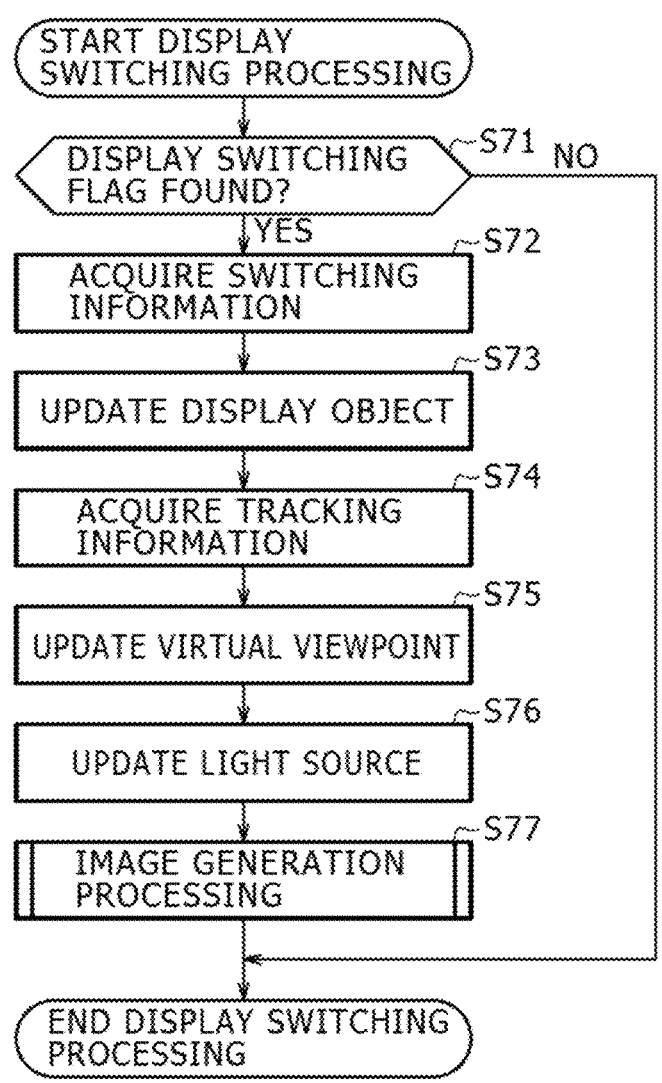
FIG. 25 is a flowchart indicative of display switching processing practiced as the fifth embodiment of the disclosure.
Figure 26:
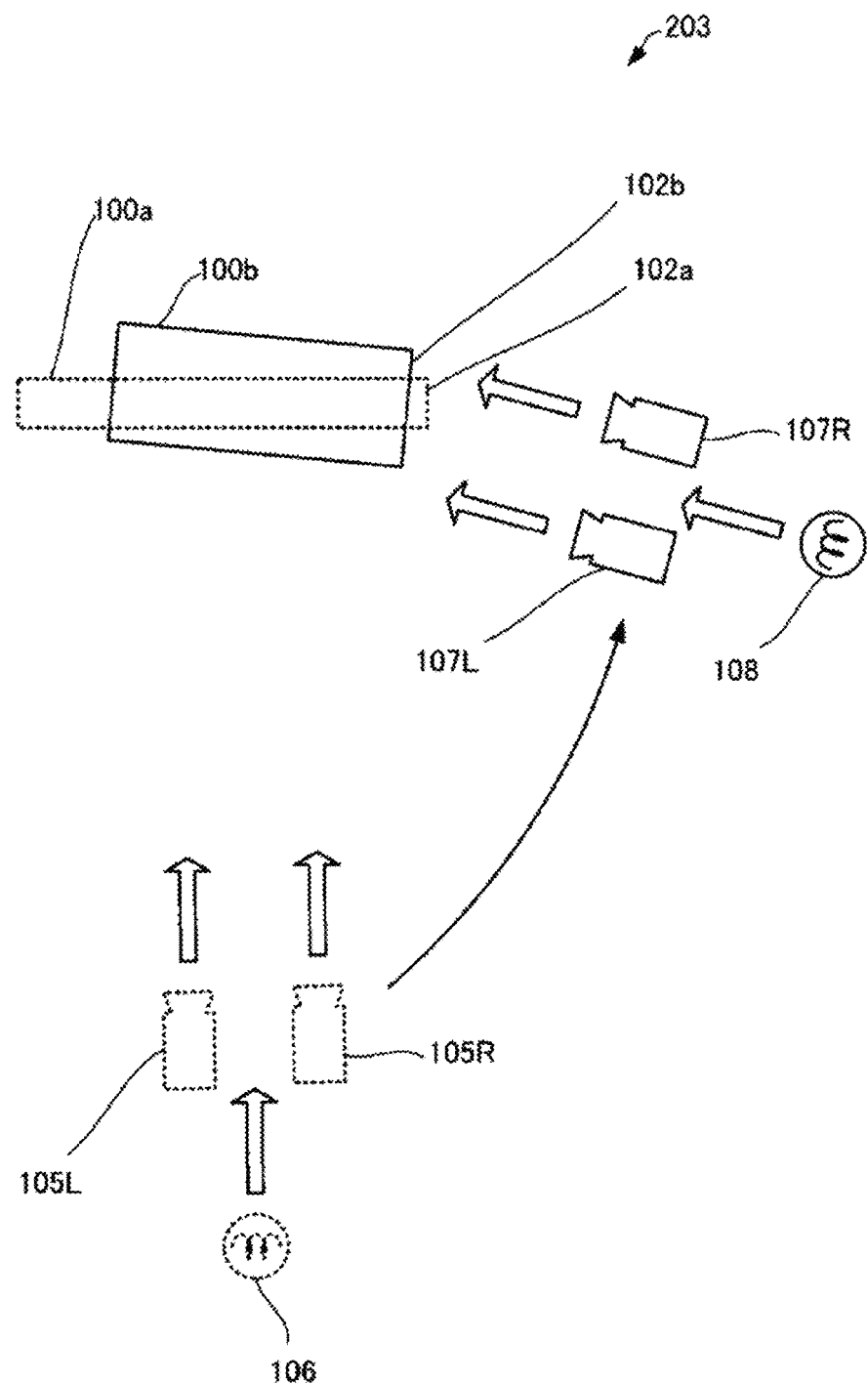
FIG. 26 is a schematic diagram illustrating how virtual viewpoints and light sources are updated, practiced as the fifth embodiment of the disclosure.

The following describes display switching processing to be executed by the information processing apparatus 30 with reference to FIG. 25 and FIG. 26. FIG. 25 is a flowchart indicative of the display switching processing practiced as the fifth embodiment of the present disclosure. FIG. 26 shows a manner of updating a virtual viewpoint and a light source of the fifth embodiment of the present disclosure. Concurrently with the execution of an application, the information processing apparatus 30 executes display switching processing. The display switching monitors a display switching flag set by switching trigger detection processing to detect the setting of display switching flag, thereby executing display switching.

[Step S71]

The information processing apparatus 30 monitors the display switching flag. If the display switching flag is found to have been set, then the information processing apparatus 30 proceeds the process to step S72; otherwise, the information processing apparatus 30 terminates the display switching processing.

[Step S72]

The information processing apparatus 30 acquires switching information.

[Step S73]

On the basis of the obtained switching information, the information processing apparatus 30 updates the display object. For example, on the basis of switching information 300, the information processing apparatus 30 sets the shape of a display object identified by identification information "001" to "thick width window," the size to "middle," the position to "x1, y1, z1," and the orientation to "dx1, dy1, dz1."

[Step S74]

The information processing apparatus 30 acquires tracking information.

[Step S75]

The information processing apparatus 30 updates the virtual viewpoint to be set on the basis of the obtained tracking information.

[Step S76]

The information processing apparatus 30 updates the light source to be set to the virtual space on the basis of the obtained tracking information.

[Step S77]

After executing the image generation processing for generating a display image, the information processing apparatus 30 terminates the display switching processing. The image generation processing executes rendering processing on the basis of a light source and a virtual viewpoint set with a display object arranged in a virtual space, thereby generating a display image. The information processing apparatus 30 synthesizes a left-eye image and a right-eye image after the generation thereof, thereby generating a display image.

An example of updating of a display object, a light source, and a virtual viewpoint before and after the execution of display switching processing is a virtual viewpoint update example 203. The virtual viewpoint update example 203 is indicative of positional relationship of display objects 100a and 100b, light sources 106 and 108, and virtual viewpoints 105L, 105R, 107L and 107R before and after display switching. It should be noted that the virtual viewpoints 105L and 107L are virtual viewpoints for generating a left-eye image and the virtual viewpoints 105R and 107R are virtual viewpoints for generating a right-eye image.

The display object 100a before display switching is switched to the display object 100b with display object shape, size, position, and orientation updated on the basis of the switching information. The light source 106 before display switching is switched to the light source 108 with position, radiation range, brightness, color, and so on updated on the basis of the tracking information. The virtual viewpoints 105L and 105R before display switching are switched to the virtual viewpoints 107L and 107R with position and orientation updated on the basis of the tracking information.

As described above, the image display apparatus 40 updates the display mode of a display object before and after display switching and updates the arrangement of a display object, a light source, and a virtual viewpoint, so that the attached information viewing plane 102b is easier for the observer 90 to observe than the attached information viewing plane 102a.

It should be noted that the image display apparatus 40 may execute only one of the updating of the display mode of a display object before and after display switching and the updating of the arrangement of a display object, a light source, and a virtual viewpoint.

It should also be noted that, when switching to the virtual viewpoints 107L and 107R, the display contents may be switched by a change larger than the detected movement of the observer 90 with a predetermined coefficient multiplied in updating the position and orientation based on the tracking information. This setup allows the image display apparatus 40 to enhance the visual recognition of the attached information viewing plane 102 without making the observer 90 to do a large movement.

The following describes a virtual space arrangement example of a display object and an image display example of a display object with reference to FIG. 27 through FIG. 30. FIG. 27 through FIG. 30 show image display and virtual space arrangement examples of a display object practiced as the fifth embodiment of the present disclosure.

A virtual space arrangement example 205 (refer to FIG. 27) is indicative of a display object 110 when the observer 90 is directly confronting the viewing plane 24 (before display switching). The display object 110 is a thin plate in shape and positioned in the depth direction from the viewing plane 24. With the display object 110, a main viewing plane 111 directed to the viewing plane 24 and an attached information viewing plane 112 to one side.

Figure 27:
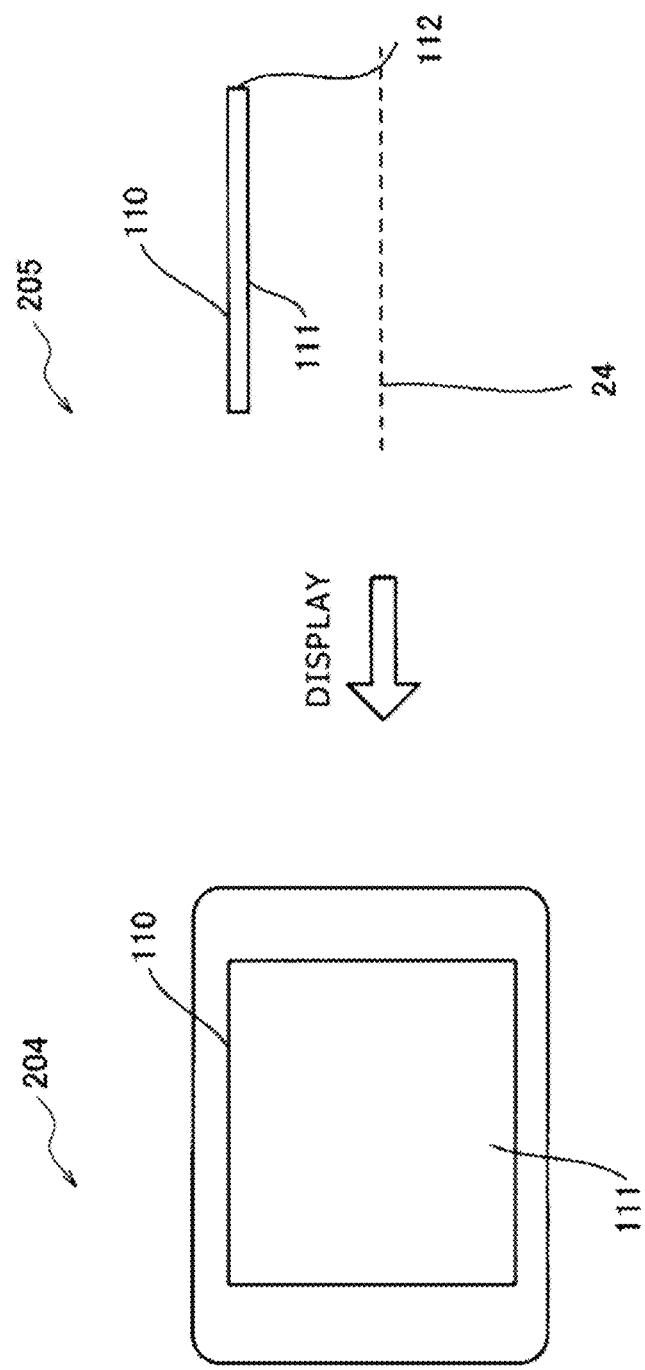
FIG. 27 is a schematic diagram illustrating one example of the image display and virtual space arrangement of a display object, practiced as the fifth embodiment of the disclosure.

The display object 110 as described above is observed by the observer 90 like an image display example 204 (refer to FIG. 27). The main viewing plane 111 of the display object 110 is in a state where the observer 90 can easily observe the main viewing plane 111 and the attached information viewing plane 112 is in a state where the observer 90 cannot observe the attached information viewing plane 112.

A virtual space arrangement example 207 (refer to FIG. 28) shows a display object 113 when the observer 90 is directly confronting the viewing plane 24 (before display switching). The display object 113 is a thin plate in shape of a trapezoid in cross section and positioned in the depth direction from the viewing plane 24. With the display object 113, a main viewing plane 114 is directed to the viewing plane 24 and an attached information viewing plane 115 is obliquely directed to the observer side.

Figure 28:
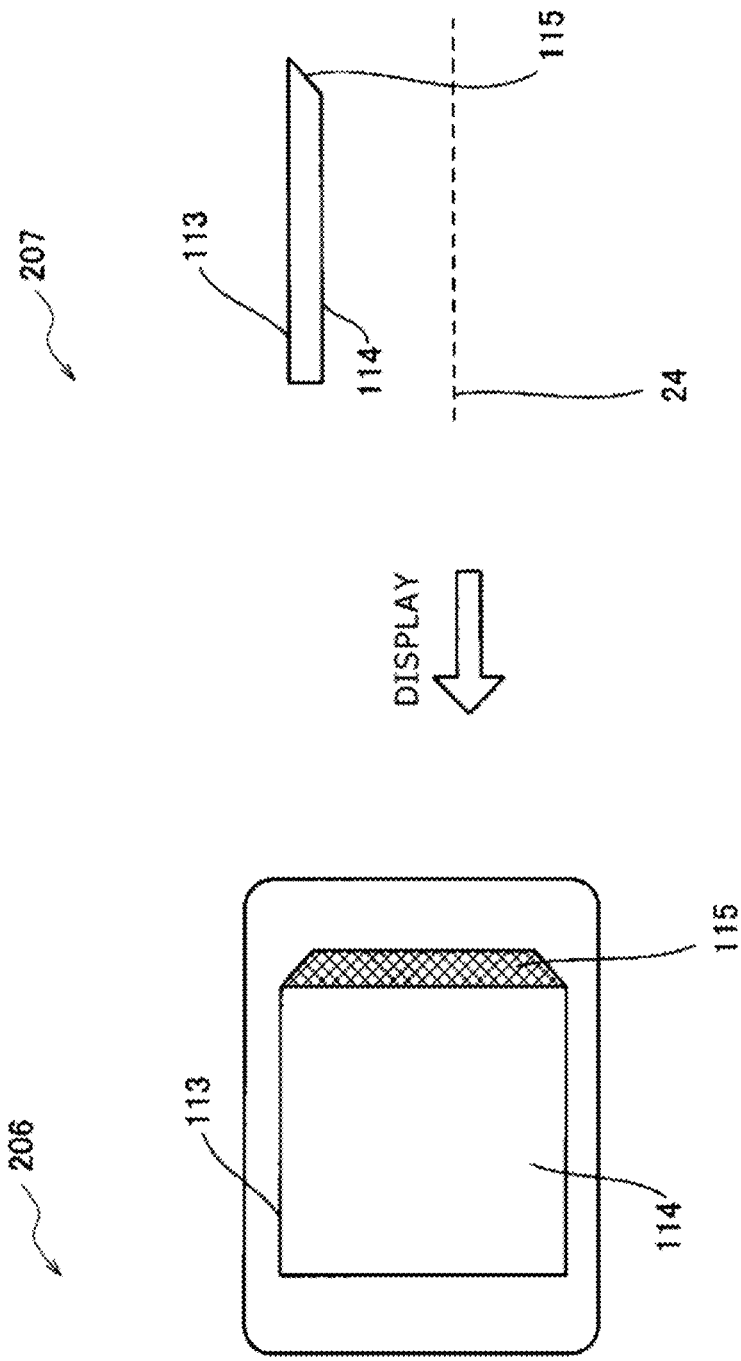
FIG. 28 is a schematic diagram illustrating another example of the image display and virtual space arrangement of a display object, practiced as the fifth embodiment of the disclosure.

The display object 113 as described above is observed by the observer 90 as an image display example 206 (refer to FIG. 28). The main viewing plane 114 of the display object 113 is easily observable by the observer 90. Although the attached information viewing plane 115 is not easily observable, the existence of the attached information viewing plane 115 can be confirmed. The attached information viewing plane 115 such as this motivates the observer 90 to execute a positional change in order to observe the attached information viewing plane 115.

When the observer 90 is not directly confronting the viewing plane 24, a virtual space arrangement example 209 (refer to FIG. 29) shows a display object 116 (after display switching). The display object 116 is a cube and positioned in the depth direction from the viewing plane 24. The display object 116 is directed to the observer with a main viewing plane 117 and an attached information viewing plane 118 directed obliquely.

Figure 29:
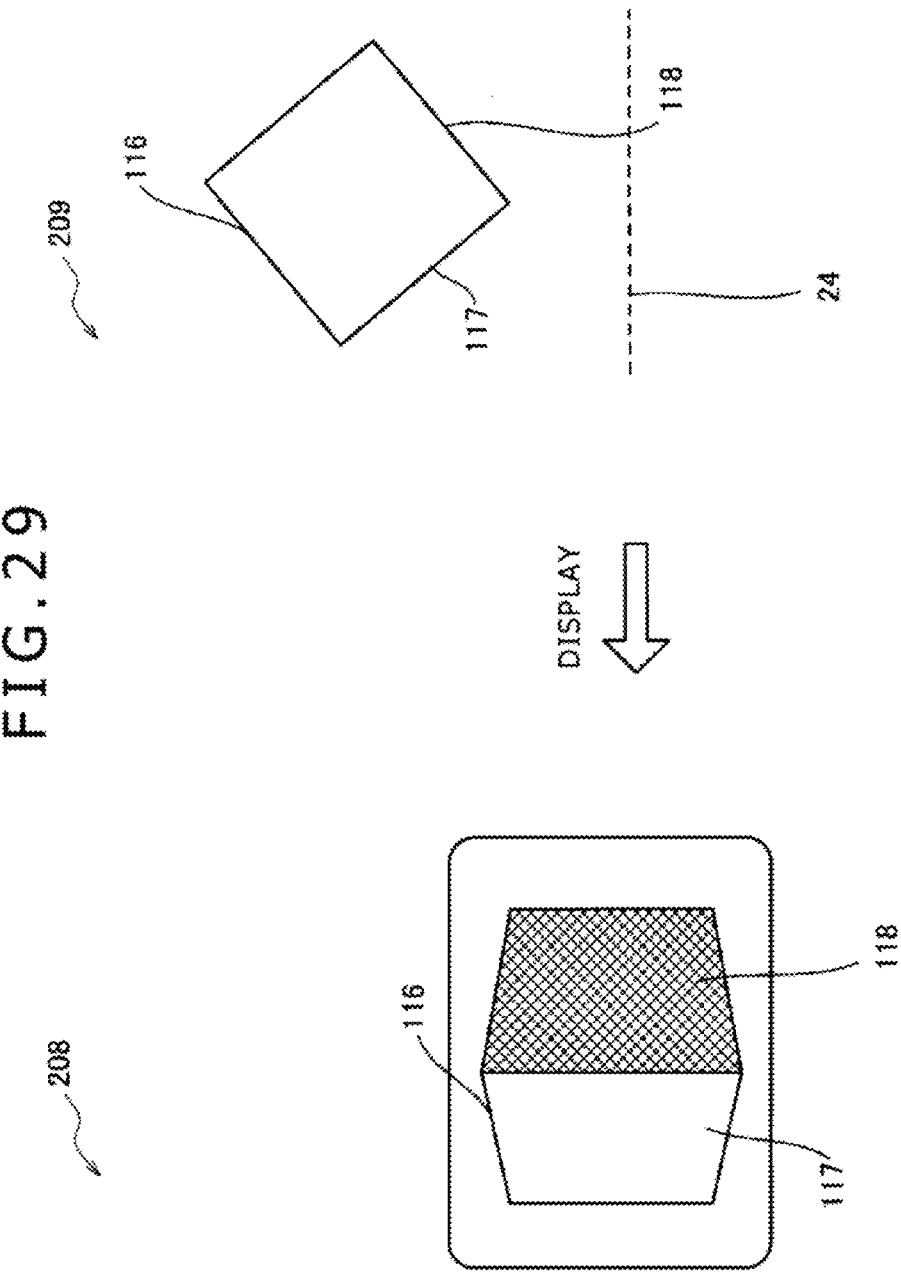
FIG. 29 is a schematic diagram illustrating still another example of the image display and virtual space arrangement of a display object, practiced as the fifth embodiment of the disclosure.

The display object 116 as described above is observed by the observer 90 as an image display example 208 (refer to FIG. 29). With the display object 116 after display switching, a display mode is updated due to a change in form and orientation and the attached information viewing plane 118 is easily observable by the observer 90.

It should be noted that, if the display object before display switching is the display object 110, then the attached information viewing plane 118 of the display object 116 can be said that the attached information viewing plane 118 has entered from non-display state of the attached information viewing plane 112 into a display state where it is easily observable by the observer 90. If the display object before display switching is the display object 113, then the attached information viewing plane 118 of the display object 116 can be said that the attached information viewing plane 118 has entered in a display state where it is easier for the observer 90 to observe than the display state of the attached information viewing plane 115.

When the observer 90 is not directly confronting the viewing plane 24 (after display switching), a virtual space arrangement example 211 (refer to FIG. 30) shows a display object 119. The display object 119 is a cube and positioned in a part directed toward the observer and a remaining part directed in the depth direction with the viewing plane 24 in between. With the display object 119, a main viewing plane 120 and an attached information viewing plane 121 are obliquely directed toward the observer.

Figure 30:
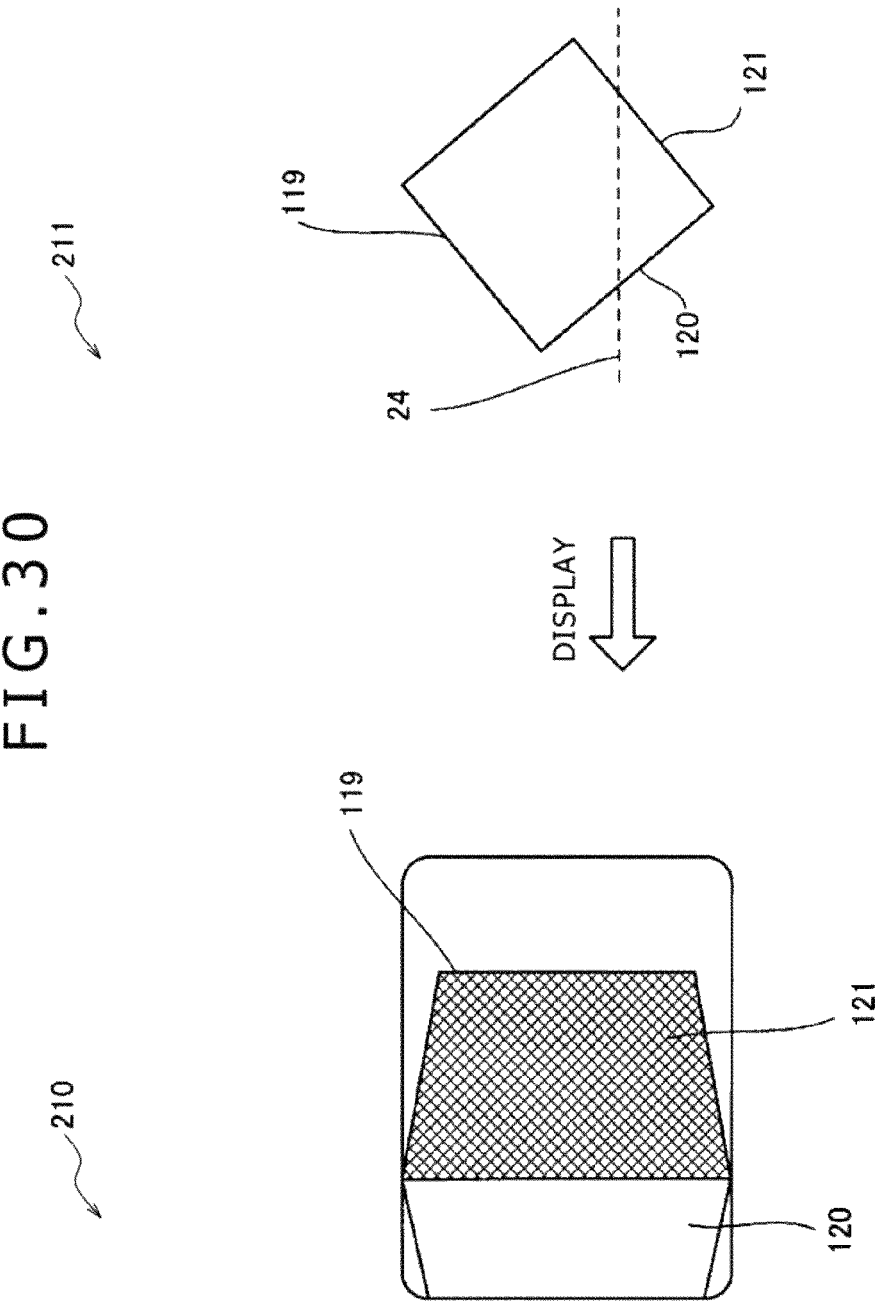
FIG. 30 a schematic diagram illustrating yet another example of the image display and virtual space arrangement of a display object, practiced as the fifth embodiment of the disclosure.

The display object 119 as described above is observed by the observer 90 as an image display example 210 (refer to FIG. 30). The display object 119 after display switching updates the display mode due to a shape change, an orientation change, or a positional change, thereby putting the additional information viewing plane 121 into a display state for the observer 90 to easily observe.

It should be noted that if the display object before display switching is the display object 110, then the additional information viewing plane 121 of the display object 119 can be said that the additional information viewing plane 121 has shifted from the non-display state of the additional information viewing plane 112 to a display state where it is easily observable by the observer 90. If the display object before display switching is the display object 113, then the additional information viewing plane 121 of the display object 119 can be said that the additional information viewing plane 121 has entered a display state where it is easier for the observer 90 to observe than the display state of the additional information viewing plane 115.

As described above, the image display apparatus 40 can change the ease of observation of the attribute information viewing plane by following the movement of the user (or the observer 90). This improvement of GUI can enhance the processing efficiency of the user by improving the operability by the user and effectively using the viewing areas.

Figure 31:
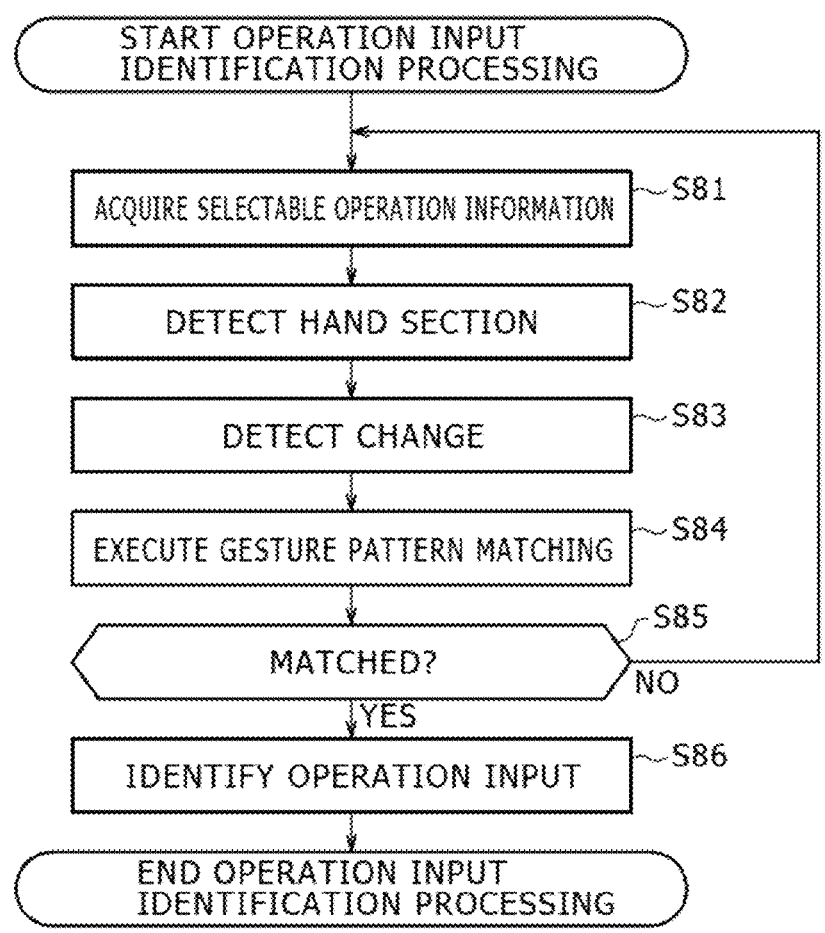
FIG. 31 is a flowchart indicative of operation input identification processing practiced as the fifth embodiment of the disclosure.

The following describes operation input identification processing to be executed by the information processing apparatus 30 with reference to FIG. 31. FIG. 31 is a flowchart indicative of the operation input identification processing practiced as the fifth embodiment of the present disclosure. Concurrently with the execution of a required application, the information processing apparatus 30 executes the operation input identification processing. The operation input identification processing detects the hand or finger of the observer 90, detects the gesture of the detected hand or finger, and identifies an operation input of an application.

[Step S81]

The information processing apparatus 30 acquires selectable operation information. The selectable operation information is information in which gesture patterns that are effective as operation inputs of a active application are defined.

[Step S82]

The information processing apparatus 30 detects the hand of the observer 90. The information processing apparatus identifies the position, orientation, and shape of the detected hand of the observer 90. The detection of the hand of the observer 90 is executed on the basis of an image taken by the imaging apparatus 22.

[Step S83]

The information processing apparatus 30 detects a time-sequence change of the hand of the observer 90.

[Step S84]

The information processing apparatus 30 makes a matching between the gesture pattern defined by the selectable operation information and the time-sequence change pattern of the hand of the observer 90.

[Step S85]

If a match is found between the gesture pattern and the time-sequence change pattern of the hand of the observer 90, the information processing apparatus 30 proceeds the process to step S86; otherwise, the information processing apparatus 30 proceeds the process to step S81.

[Step S86]

The information processing apparatus 30 identifies the operation input corresponding to the matched gesture pattern from the selectable operation information and terminates the operation input identification processing.

Figure 32:
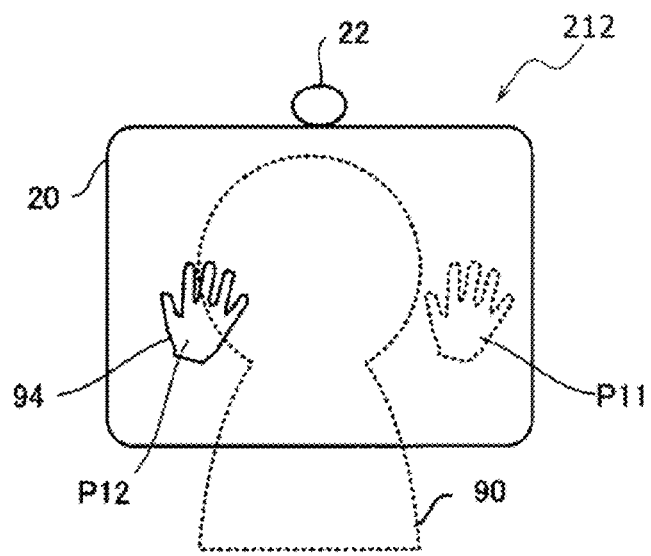
FIG. 32 is a schematic diagram illustrating one example of gesture input practiced the fifth embodiment of the disclosure.

The following describes a specific example of gesture input with reference to FIG. 32. FIG. 32 shows one example of gesture input practiced as the fifth embodiment of the present disclosure.

It should be noted that the 3D image display apparatus 20 practiced as the fifth embodiment of the present disclosure has an imaging apparatus 22 on the frame section or the peripheral section of the viewing plane. The imaging apparatus 22 takes an image of the observer 90. The image taken by the imaging apparatus 22 is used for identifying the position of the observer 90 to detect a positional change. Also, the image taken by the imaging apparatus 22 can be used for gesture input in addition to the detection of a positional change.

It should also be noted that a subject of image taking by the imaging apparatus 22 may be all of the observer 90 or a part or parts of the body of the observer 90. For example, the body trunk of the observer 90 becomes the subject of image taking in the case of body tracking. The head of the observer 90 becomes the subject of image taking in the case of head tracking. The arm and the hand of the observer 90 become subjects of image taking in the case of arm tracking and hand tracking, respectively. The face of the observer 90 becomes the subject of image taking in the face of face tracking. Left eye EL, left pupil, right eye ER, and right pupil of the observer 90 become subjects of image taking in the case of eye tracking (including sight line detection).

A gesture input example 212 is indicative of a gesture input example in which the hand 94 of the observer 90 has moved from position P11 to position P12. By detecting the hand 94 at position P11 and then at position P12, the information processing apparatus 30 detects that the amount of a change in the hand 94 within a predetermined time is equivalent to a predetermined distance in a predetermined direction (the hand has moved 20 cm to the left, for example). If the detected change pattern is found matching a predetermined gesture pattern, the information processing apparatus 30 accepts a predetermined operation input.

In addition, the gesture input may detect that the hand 94 of the observer 90 has rotated by a predetermined amount. For example, by detecting the hand 94 including the positional relation of the finger and then detecting the rotation by making a comparison between the positional relations of the finger of the hand 94, the information processing apparatus 30 detects that the amount of a change in the hand 94 within a predetermined time is equivalent to a predetermined angles in a predetermined direction (30 degrees counterclockwise, for example). When the detected change pattern is found matching a predetermined gesture pattern, the information processing apparatus 30 accepts a predetermined operation input.

Further, the gesture input may detect the proximity of the hand 94 of the observer 90 by a predetermined amount. For example, the information processing apparatus 30 detects that the amount of a change in the hand 94 within a predetermined time is equivalent to a predetermined distance in a predetermined direction (10 cm moved in the proximity direction, for example). When a match is found between the detected change pattern and a predetermined gesture pattern, the information processing apparatus 30 accepts a predetermined operation input.

It should be noted that, in addition to the examples shown above, the gesture input may be one that detects a change in inclination (a change of the orientation of the palm, for example) or a change in shape (shut fist or open fist, for example).

It should also be noted that, in the description made above, the gesture input by use of the hand 94 is used for example; however, in addition to the hand 94, other body parts (the head and the face, for example) of the observer 90 may be used for gesture. Further, the gesture input may include the sight line input in which the movement of the left pupil or the right pupil is detected. Besides, the operation input based on gestures may handle an operation input equivalent to a mouse operation or a touch panel operation.

It should be noted that the gesture input may be one in which a change in the observer 90 is detected, display switching is executed, and then a gesture input is accepted as an effective input. In addition, the gesture input may be limited to one in which the attached information viewing plane is handled. This configuration allows the image display apparatus 40 facilitate for the user to understand a gesture input effective state or an object with which gesture input is effective. Moreover, the image display apparatus 40 can change the operation contents in which a right click operation is executed through the mouse 39 to the display switching based on the movement of the observer 90 instead of the right click input and the gesture input instead of the pointing, selection and enter operation through the mouse 39. Consequently, the image display apparatus 40 can improve the operability by the user, thereby enhancing the processing efficiency of the user.

The Sixth Embodiment

Figure 33:
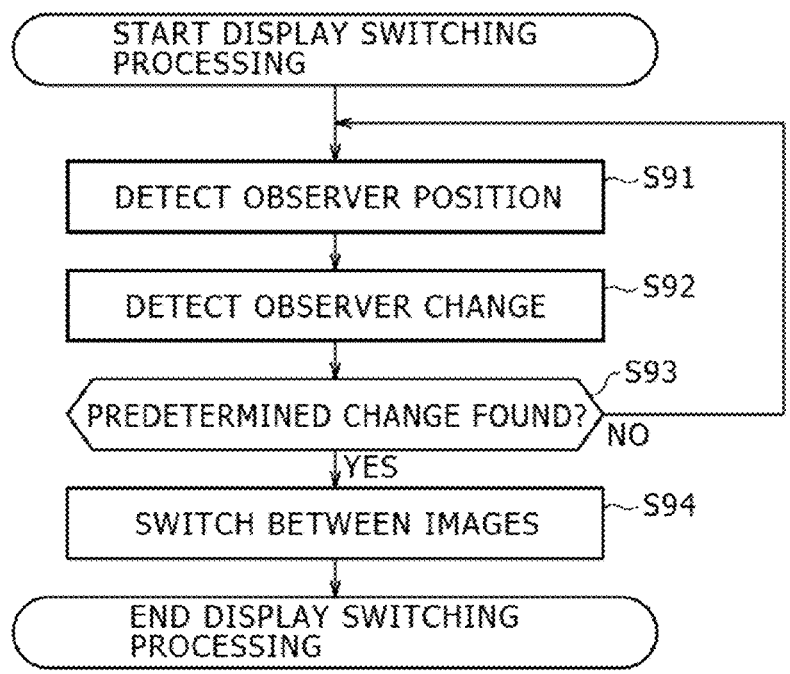
FIG. 33 is a flowchart indicative of display switching processing practiced as a sixth embodiment of the disclosure.

The following describes a display switching processing practiced as the sixth embodiment of the present disclosure with reference to FIG. 33. FIG. 33 is a flowchart indicative of the display switching processing practiced as the sixth embodiment of the present disclosure. The display switching processing practiced as the sixth embodiment of the present disclosure differs from the display switching processing practiced as the fifth embodiment of the present disclosure in that display images are not generated on the basis of switching information but switching is made to prepared display images. In addition, display switching is executed including the positional detection of the observer 90, so that the switching trigger detection processing of the fifth embodiment is not executed in the sixth embodiment. Like the fifth embodiment, the information processing apparatus 30 executes the display switching processing concurrently with the execution of a required application.

[Step S91]

The information processing apparatus 30 executes the positional detection of the observer 90 on the basis of an input from an imaging apparatus 22.

[Step S92]

The information processing apparatus 30 detects a predetermined change in the position of the observer 90.

[Step S93]

If a predetermined change in the position of the observer 90 has been detected, the information processing apparatus 30 proceeds the process to step S94; otherwise, the information processing apparatus 30 proceeds the process to step S91.

[Step S94]

The information processing apparatus 30 executes switching to a display image with which an attached information viewing plane is easy to observe, thereby terminating the display switching processing.

By preparing a first display image and a second display image in which an attached information viewing plane can be observed easier than the first display image, the information processing apparatus 30 can easily execute switching to the display image in which the attached information viewing plane can be observed more easily.

It should be noted that the image display apparatus 40 has the 3D image display apparatus 20 for displaying images of two viewpoints (a right-eye image and a left-eye image); however, it is also practicable to have a 3D image display apparatus based on multiple viewpoints. In this case, the image display apparatus 40 displays the images before and after switching to be displayed on the 3D image display apparatus 20 onto the 3D image display apparatus based on multiple viewpoints in correspondence with different viewpoints.

It should also be noted that the processing functions described above can be realized by use of a computer. In this case, programs written with the processing contents of the functions of each apparatus are provided. Executing these programs on a computer realizes the above-mentioned functions on the computer. The programs written with the processing contents can be recorded to recording media that can be read by the computer.

Programs can be delivered for sale in a DVD (Digital Versatile Disc), a CD-ROM (Compact Disc Read Only Memory), or other portable recording media. It is also practicable to store programs in a storage apparatus of a server computer and transfer the stored programs from the server computer to other computers via a network.

A computer for executing programs stores the programs recorded in and transferred from a portable recording media or programs transferred from a server computer into a storage apparatus of the computer. Then, the computer reads programs from the storage apparatus thereof and executes the processing as instructed by these programs.

It should be noted that the technology disclosed herein can also take a configuration described below.

(1) An information processing apparatus including:

a display output block configured to output email information display to a display apparatus on which a three-dimensional image is observable by an observer on the basis of binocular parallax;

an input block configured to receive a predetermined input operation; and a switching block configured to switch, on the basis of the input operation, display states of the email information display from a first display state to a second display state differing from the first display state in a depth position in the display apparatus.

(2) The information processing apparatus according to (1) above, wherein the email information display is for displaying a plurality of email messages, and the switching block switches the first display state to the second display state in which the plurality of email messages are arranged at the depth position corresponding to attribute information of each of the plurality of email messages.

(3) The information processing apparatus according to (2) above, wherein
the switching block divides the plurality of email messages into predetermined groups in accordance with the attribute information of each of the plurality of email messages to arrange the plurality of email messages at a plurality of preset depth positions in unit of the groups.

(4) The information processing apparatus according to (3) above, wherein
the switching block switches the first display state to the second display state by changing the plurality of depth positions set in unit of the groups.

(5) The information processing apparatus according to (1) above, wherein
the email information display is for displaying email contents by dividing the email contents into a plurality of areas and
the switching block switches the first display state to the second display state in which the plurality of areas are arranged at the plurality of depth positions corresponding to the attribute information of each of the plurality of areas.

(6) The information processing apparatus according to (5) above, wherein
the attribute information is a quote depth of the email contents.

(7) The information processing apparatus according to (5) or (6) above, wherein
the switching block divides the plurality of areas into predetermined groups in accordance with the attribute information of each of the plurality of areas to arrange the plurality of areas at a plurality of preset depth positions in unit of the groups.

(8) The information processing apparatus according to (7) above, wherein
the switching block switches the first display state to the second display state by changing the plurality of depth positions set in unit of the groups.

(9) The information processing apparatus according to any one of (1) through (8) above, wherein
the switching block uses a depth position of a focused display element in the second display state as a viewing plane.

(10) The information processing apparatus according to any one of (1) through (8) above, wherein
the switching block makes a depth position of a focused display element in the second display state substantially the same as a depth position of a periphery display section.

(11) The information processing apparatus according to any one of (1) through (10) above, wherein
the input block accepts a selective operation by a slide bar of a focused display element in the second display state.

(12) The information processing apparatus according to (1) above, wherein
the display output block outputs main display for handling email and attached information display for displaying attached information associated with the main display as the email information display;
the input block has a positional information input block configured to enter positional information of the observer who makes observation on the display apparatus and a change detection block configured to detect a change in the positional information; and
the switching block switches display states of the attached information display from the first display state to the second display state on the basis of the detection of the change.

(13) The information processing apparatus according to (12) above, wherein
the attached information is operation information associated with an operation of the main display.

(14) The information processing apparatus according to (13) above, further including:
a gesture detection block configured to detect a selective operation associated with the operation information from a gesture made by the observer in the second display state.

(15) The information processing apparatus according to (12) above, wherein
the attached information is information associated with an email usage amount.

(16) The information processing apparatus according to (12) through (15) above, wherein
the attached information is non-display in the first display state.

(17) The information processing apparatus according to (12) through (16) above, wherein
the main display and the attached information display are displayed on different faces of a display object made of a polyhedron.

(18) The information processing apparatus according to (12) through (17) above, wherein,
in switching from the first display state to the second display state, the switching block switches virtual viewpoints of the display object from a first virtual viewpoint to a second virtual viewpoint.

(19) An image display apparatus including:
a three-dimensional image display block configured to display email information in a three-dimensional image observable by an observer on the basis of binocular parallax;
an input block configured to accept a predetermined input operation; and
a switching block configured to switch, on the basis of the input operation, display states of the email information display from a first display state to a second display state differing from the first display state in a depth position in the image display apparatus.

(20) An information processing method including:
outputting email information display to a display apparatus on which a three-dimensional image is observable by an observer on the basis of binocular parallax;
receiving a predetermined input operation; and
switching, on the basis of the input operation, display states of the email information display from a first display state to a second display state differing from the first display state in a depth position in the display apparatus.

While preferred embodiments of the present disclosure have been described using specific terms, such description is for illustrative purpose only, and it is to be understood that changes and variations may be made without departing from the spirit or scope of the following claims.

Further, preferred embodiments of the present disclosure may be modified and changed in many forms and manners by those skilled in the art and are not limited to the accurate configurations and the applications examples described above.

What is claimed is:
1. An information processing apparatus comprising:
a display output block configured to output email information display to a display apparatus on which a three-dimensional image is observable by an observer on the basis of binocular parallax;
an input block configured to receive a predetermined input operation; and a switching block configured to switch, on the basis of said input operation, display states of said email information display from a first display state to a second display state differing from said first display state in a depth position in said display apparatus, wherein said email information display is for displaying a plurality of email messages, and wherein the information processing apparatus enables (i) a plurality of layers to be set, in which each layer corresponds to a respective depth position displayed in a depth direction from a viewing plane of the display apparatus, wherein a respective parallax amount is set between a left-eye image and a right-eye image corresponding to each layer, (ii) said plurality of email messages to be respectively arranged at the depth positions corresponding to attribute information of each email message, and (iii) said plurality of email messages respectively arranged at the depth positions to be respectively reallocated at reallocated depth positions with reference to a focused email message.

2. The information processing apparatus according to claim 1, wherein said switching block uses a depth position of a focused display element in said second display state as the viewing plane.

3. The information processing apparatus according to claim 1, wherein said switching block makes a depth position of a focused display element in said second display state substantially the same as a depth position of a periphery display section.

4. The information processing apparatus according to claim 1, wherein said input block accepts a selective operation by a slide bar of a focused display element in said second display state.

5. The information processing apparatus according to claim 1, wherein
said display output block outputs a main display for handling email and attached information display for displaying attached information associated with said main display as said email information display;
said input block has a positional information input block configured to enter positional information of said observer who makes observation on said display apparatus and a change detection block configured to detect a change in said positional information; and
said switching block switches display states of said attached information display from said first display state to said second display state on the basis of the detection of said change.

6. The information processing apparatus according to claim 5, wherein said attached information is operation information associated with an operation of said main display.

7. The information processing apparatus according to claim 6, further comprising:
a gesture detection block configured to detect a selective operation associated with said operation information from a gesture made by said observer in said second display state.

8. The information processing apparatus according to claim 5, wherein said attached information is information associated with an email usage amount.

9. The information processing apparatus according to claim 5, wherein said attached information is not displayed in said first display state.

10. The information processing apparatus according to claim 5, wherein said main display and said attached information display are displayed on different faces of a display object made of a polyhedron.

11. The information processing apparatus according to claim 5, wherein, in switching from said first display state to said second display state, said switching block switches virtual viewpoints of a display object from a first virtual viewpoint to a second virtual viewpoint.

12. An image display apparatus comprising:
a three-dimensional image display block configured to display email information in a three-dimensional image observable by an observer on the basis of binocular parallax;
an input block configured to accept a predetermined input operation; and
a switching block configured to switch, on the basis of said input operation, display states of said email information display from a first display state to a second display state differing from said first display state in a depth position in said image display apparatus,
wherein said email information display is for displaying a plurality of email messages, and
wherein the image display apparatus enables (i) a plurality of layers to be set, in which each layer corresponds to a respective depth position displayed in a depth direction from a viewing plane of the image display apparatus, wherein a respective parallax amount is set between a left-eye image and a right-eye image corresponding to each layer, (ii) said plurality of email messages to be respectively arranged at the depth positions corresponding to attribute information of each email message, and (iii) said plurality of email messages respectively arranged at the depth positions to be respectively reallocated at reallocated depth positions with reference to a focused email message.

13. An information processing method comprising:
outputting email information display to a display apparatus on which a three-dimensional image is observable by an observer on the basis of binocular parallax;
receiving a predetermined input operation;
switching, on the basis of said input operation, display states of said email information display from a first display state to a second display state differing from said first display state in a depth position in said display apparatus, wherein said email information display is a plurality of email messages; and
enabling (i) a plurality of layers to be set, in which each layer corresponds to a respective depth position displayed in a depth direction from a viewing plane of the display apparatus, wherein a respective parallax amount is set between a left-eye image and a right-eye image corresponding to each layer, (ii) said plurality of email messages to be respectively arranged at the depth positions corresponding to attribute information of each email message, and (iii) said plurality of email messages respectively arranged at the depth positions to be respectively reallocated at reallocated depth positions with reference to a focused email message.

* * * * *